United States Patent [19]
Hötten et al.

[11] Patent Number: 5,807,713
[45] Date of Patent: Sep. 15, 1998

[54] DNA ENCODING GROWTH/ DIFFERENTIATION FACTOR

[75] Inventors: Gertrud Hötten, Bochum; Helge Neidhardt, Marburg; Rolf Bechtold, Heidelberg; Jens Pohl, Hambrücken, all of Germany

[73] Assignee: Biopharm Gesellschaft zur Biotechnologischen Entwicklung, Heidelberg, Germany

[21] Appl. No.: 482,577

[22] Filed: Jun. 7, 1995

Related U.S. Application Data

[63] Continuation-in-part of Ser. No. 289,222, filed as PCT/EP93/00350 Feb. 12, 1993.

[30] Foreign Application Priority Data

| Feb. 12, 1992 | [EP] | European Pat. Off. .............. 92102324 |
| Jul. 1, 1994 | [DE] | Germany .......................... 44 23 190.3 |
| Mar. 27, 1995 | [DE] | Germany ....................... 195 11 243.1 |

[51] Int. Cl.⁶ ............................ C12N 15/19; C07K 14/52
[52] U.S. Cl. .................. 435/69.5; 435/71.1; 435/172.3; 435/252.3; 435/320.1; 435/325; 435/419; 536/23.1; 536/23.5
[58] Field of Search ................................. 435/69.5, 172.3, 435/240.2, 252.3, 320.1, 71.1, 325, 419, 254.1; 536/23.1, 23.5; 935/11, 22, 66, 68, 67, 71, 72

[56] References Cited

FOREIGN PATENT DOCUMENTS

| 0 222 491 | 10/1986 | European Pat. Off. . |
| 93/16099 | 8/1993 | WIPO . |
| PCT/EP 95/02552 | 11/1995 | WIPO . |

OTHER PUBLICATIONS

Hötten et al., "Cloning of a New Member of the TGF-β Family: A Putative New Activin $\beta_c$ Chain", Biochem. & Biophys. Res. Comm., vol. 206, No. 2, 1995.

*Primary Examiner*—John Ulm
*Assistant Examiner*—Prema Mertz
*Attorney, Agent, or Firm*—Nikaido Marmelstein Murray & Oram LLP

[57] ABSTRACT

The invention concerns a protein of the TGF-β family, the DNA coding therefor and a pharmaceutical composition containing such a protein.

6 Claims, 5 Drawing Sheets

Fig. 1

|  | 10 | 20 | 30 | 40 |
|---|---|---|---|---|
| MP121 | CCRQEFFVDF | REIGWHDWII | OPEGYAMNFC | IGQCPLHIAG |
| INHIB βA | CCKKQFFVSF | KDIGWNDWII | APSGYHANYC | EGECPSHIAG |
| INHIB βB | CCRQQFFIDF | RLIGWNCWII | APTGYYGNYC | EGSCPAYLAG |
| INHIB α | CHRVALNISF | QELGWERWIV | YPPSFIFHYC | HGGCGLHIP- |
|  | ✱+++ ++++✱ | +++✱✱ +✱✱+ | ✱ ++ + ✱ | ✱ ✱++++++ |

|  | 50 | 60 | 70 | 80 |
|---|---|---|---|---|
| MP121 | MPGIAASFHT | AVLNLLKANT | AAGTTGGGSC | C--VPTARRP |
| INHIB βA | TSGSSLSFHS | TVINHYRMRG | HSPFANLKSC | C--VPTKLRP |
| INHIB βB | VPGSASSFHT | AVVNQYRMRG | LNP-GTVNSC | C--IPTKLST |
| INHIB α | ---PNLSLPV | PGAPPTPAQP | YSLLPGAQPC | CAALPGTMRP |
|  | ++ + ✱+++ | ++ + + | + +✱ ✱ +✱+ ++ |  |

|  | 90 | 100 | 110 |  |
|---|---|---|---|---|
| MP121 | LSLLYYDRDS | NIVKTD-IPD | MVVEACGCS | SEQ ID NO: 24 |
| INHIB βA | MSMLYYDDGQ | NIIKKD-IQN | MIVEECGCS | SEQ ID NO: 25 |
| INHIB βB | MSMLYFDDEY | NIVKRD-VPN | MIVEECGCA | SEQ ID NO: 26 |
| INHIB α | LHVRTTSDGG | YSFKYETVPN | LLTQHCACI | SEQ ID NO: 27 |
|  | ++ ++++ | +++✱ + ++ | + ++ ✱+✱+ |  |

Fig. 2a

| | EcoRI Nco I | |
|---|---|---|
| OD | ATGAATTCCCATGGACCTGGGCTGGMAKGAMTGGAT | SEQ ID NO: 28 |
| BMP 2 | ACGTGGGGTGGAATGACTGGAT | SEQ ID NO: 29 |
| BMP 3 | ATATTGGCTGGAGTGAATGGAT | SEQ ID NO: 30 |
| BMP 4 | ATGTGGGCTGGAATGACTGGAT | SEQ ID NO: 31 |
| BMP 7 | ACCTGGGCTGGCAGGACTGGAT | SEQ ID NO: 32 |
| TGF-β1 | AGGACCTCGGCTGGAAGTGGAT | SEQ ID NO: 33 |
| TGF-β2 | GGGATCTAGGGTGGAAATGGAT | SEQ ID NO: 34 |
| TGF-β3 | AGGATCTGGGCTGGAAGTGGGT | SEQ ID NO: 35 |
| INHIBIN α | AGCTGGGCTGGGAACGGTGGAT | SEQ ID NO: 36 |
| INHIBIN βA | ACATCGGCTGGAATGACTGGAT | SEQ ID NO: 37 |
| INHIBIN βB | TCATCGGCTGGAACGACTGGAT | SEQ ID NO: 38 |

Fig. 2b

| | EcoRI | |
|---|---|---|
| OID | ATGAATTCGAGCTGCGTSGGSRCACAGCA | SEQ ID NO: 39 |
| BMP 2 | GAGTTCTGTCGGGACACAGCA | SEQ ID NO: 40 |
| BMP 3 | CATCTTTTCTGGTACACAGCA | SEQ ID NO: 41 |
| BMP 4 | CAGTTCAGTGGGCACACAACA | SEQ ID NO: 42 |
| BMP 7 | GAGCTGCGTGGGCGCACAGCA | SEQ ID NO: 43 |
| TGF-β1 | CAGCGCCTGCGGCACGCAGCA | SEQ ID NO: 44 |
| TGF-β2 | TAAATCTTGGGACACGCAGCA | SEQ ID NO: 45 |
| TGF-β3 | CAGGTCCTGGGGCACGCAGCA | SEQ ID NO: 46 |
| INHIBIN α | CCCTGGGAGAGCAGCACAGCA | SEQ ID NO: 47 |
| INHIBIN βA | CAGCTTGGTGGGCACACAGCA | SEQ ID NO: 48 |
| INHIBIN βB | CAGCTTGGTGGGAATGCAGCA | SEQ ID NO: 49 |

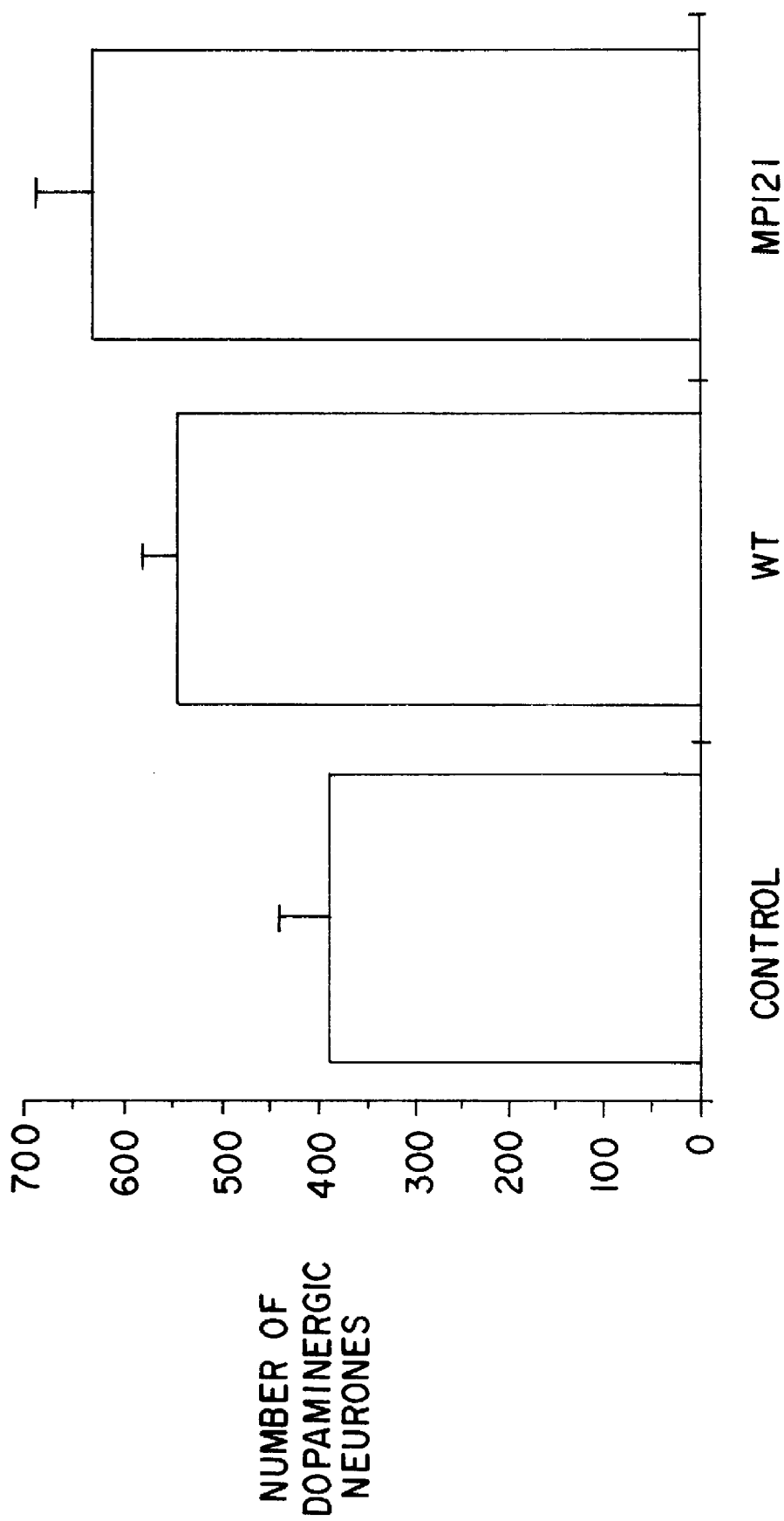

DNA ENCODING GROWTH/ DIFFERENTIATION FACTOR

CROSS REFERENCE TO RELATED APPLICATION

This is a continuation-in-part of U.S. patent application Ser. No. 08/289,222, filed as PCT/EP93/00350 Feb. 12, 1993.

DESCRIPTION

The present invention concerns a new growth/ differentiation factor of the TGF-β family and DNA sequences coding therefor.

The BMP-, TGF- and inhibin-related proteins are members of the TGF-β family of growth factors (Roberts and Sporn, Handbook of Experimental Pharmacology 95, 419–472 (1990)). They are relevant for a wide range of medical therapeutic methods and applications. These factors are suitable for methods relating to wound healing and tissue regeneration. Moreover several members of the TGF-β family induce tissue growth for example the growth of bones.

Wozney (Progress in Growth Factor Research 1 (1989), 267–280) and Vale et al. (Handbook of Experimental Pharmacology 95 (1990), 211–248) describe various growth factors for example those which are related to the BMP and the activin/inhibin group. The members of this group have significant structural similarities. The precursor of the protein is composed of an amino-terminal signal sequence, a propeptide sequence and a carboxy-terminal sequence of 110 to 140 amino acids which is cleaved from the precursor and represents the mature protein. Furthermore its members are defined by an amino acid sequence homology. The mature protein contains the sequences that are conserved most, in particular seven cysteine residues which ale conserved among the family members. The TGF-β-like proteins are multifunctional, hormonally active growth factors. They also have related biological activities for example chemotactic attraction of cells, promotion of cell differentiation and tissue-inducing capabilities. EP O 222 491 A1 discloses sequences of inhibin alpha and beta chains.

On the whole the proteins of the TGF-β family show differences in their structure which leads to considerable variations in their exact biological function. In addition they are found in a wide range of different types of tissues and stages of development. As a consequence they may be different with regard to their exact function e.g. the required cellular physiological environment, their life span, their target areas, their requirements for auxiliary factors and their resistance to degradation. Although numerous proteins that show tissue-inductive potential have been described, their natural functions in the organism and—even more importantly—their medical relevance still has to be researched in detail. It can in all probability be assumed that there are still unknown members of the TGF-β family which are of importance for the differentiation/induction of various types of tissue. However, a major difficulty in the isolation of these new TGF-β-like proteins is that their functions cannot yet be described precisely enough to develop a highly discriminating bioassay. On the other hand the expected nucleotide sequence homology to known members of the family is too small to enable screening by classical nucleic acid hybridization techniques. Nevertheless the further isolation and characterization of new TGF-β-like proteins is urgently required in order to provide further inducing and differentiation proteins which fulfil all medical requirements. These factors could be used medically in healing injuries and treating degenerative diseases of various tissues.

A nucleotide and amino acid sequence for the TGF-β protein MP-121 is given in the patent application PCT/EP93/00350 in which a major part of the sequence corresponding to the mature protein is stated. The complete sequence of the propeptide MP-121 is not disclosed.

The underlying object of the present invention is to provide DNA sequences which code for new members of the TGF-β protein family with mitogenic and/or differentiation-inductive potential. The object of the present invention is in particular to provide the complete DNA and amino acid sequence of the TGF protein MP-121.

This object is achieved by a DNA molecule that codes for a protein of the TGF-β family and which comprises (a) the part coding for the mature protein and if necessary further functional parts of the nucleotide sequence shown in SEQ ID NO. 1, (b) a nucleotide sequence corresponding to the sequence from (a) within the scope of the degeneracy of the genetic code, (c) a nucleotide sequence corresponding to an allelic derivative of one of the sequences from (a) and (b) or (d) a sequence which differs from sequence (a) due to the fact that it originates from other vertebrates (e) a sequence hybridizing with one of the sequences from (a), (b), (c) or (d)

provided that a DNA molecule according to (e) contains at least the part coding for a mature protein of the TGF-β family.

Further embodiments of the present invention concern the subject matter of claims 2 to 10. Other features and advantages of the invention emerge from the description of the preferred embodiments. The sequence protocols and drawings are now briefly described.

SEQ ID NO. 1 shows the complete nucleotide sequence of the DNA coding for the human TGF-β protein MP-121. The ATG start codon begins at nucleotide 128. The start of the complete mature protein particularly preferably begins at nucleotide 836.

SEQ ID NO. 2 shows the complete amino acid sequence of the preproprotein of the human TGF-β protein MP-121 which was derived from the nucleotide sequence shown in SEQ ID NO. 1. The start of the mature protein is preferably in the region of amino acids 217–240, particularly preferably at amino acid 236 or 237 and most preferably at amino acid 237.

SEQ ID NO.3 shows the complete nucleotide sequence of the DNA coding for the TGF-β protein MP121 from the mouse. The coding region begins at the ATG start codon at nucleotide 131 and ends at the stop codon beginning at position 1187. The start of the mature protein preferably begins at nucleotide 839. A ca. 5.5 kb large intron is located in the genomic DNA between position 446 and 447.

SEQ ID NO. 4 shows the complete amino acid sequence of the preprotein of the TGF-β protein MP121 from the mouse which has been derived from the nucleotide sequence shown in SEQ ID NO. 3. The mature protein begins in the region of amino acids 217–240 in analogy to the human MP121 of SEQ ID NO.2. It is most preferred when the mature protein starts at amino acid 237 so that the mature part consists of 116 amino acids as in the human MP121. Members of the TGF-β family are frequently cleaved behind a RXXR cleavage site in order to separate the mature part from the precursor (see Özkaynak et al., J. Biol. Chem. 267, 25220–25227 (1992) and the literature cited therein). In the case of MP121 from the mouse it is also conceivable that the beginning of the mature protein is at least sometimes at amino acid 236.

SEQ ID NO.5 shows the nucleotide sequence of the human MP121 gene at the exon/intron junctions. The nucleotides from both exons are marked by capital letters those of the intron by small letters.

BRIEF DESCRIPTION OF THE DRAWINGS

FIG. 1 shows a comparison of the amino acid sequence of human MP-121 with some members of the TGF-β family (inhibin α and β chains) starting at the first of the seven conserved cysteine residues. * denotes that the amino acid is the same in all compared proteins; + denotes that the amino acid corresponds in at least one of the proteins compared to human MP-121.

FIG. 2 shows the nucleotide sequences of the oligonucleotide primers which were used in the present invention and a comparison of these sequences with known members of the TGF-β family. M denotes A or C, S denotes C or G, R denotes A or G and K denotes G or T. FIG. 2a shows the sequence of primer OD, FIG. 2b shows the sequence of primer OID.

1: E. coli cells transformed with pBP4MP121 His under reducing conditions (1% Ô-mercaptoethanol)

2: Cell culture supernatant of NIH-3T3 cells after infection with recombinant viruses (with inserted MP121 cDNA) under reducing conditions (1% Ô-mercaptoethanol)

3: Cell culture supernatant of NIH-3T3 cells after infection with recombinant viruses (with inserted MP121 cDNA) under non-reducing conditions M: prestained protein molecular weight markers having the stated apparent molecular weights (Gibco BRL #26041-020)

Figure 4:
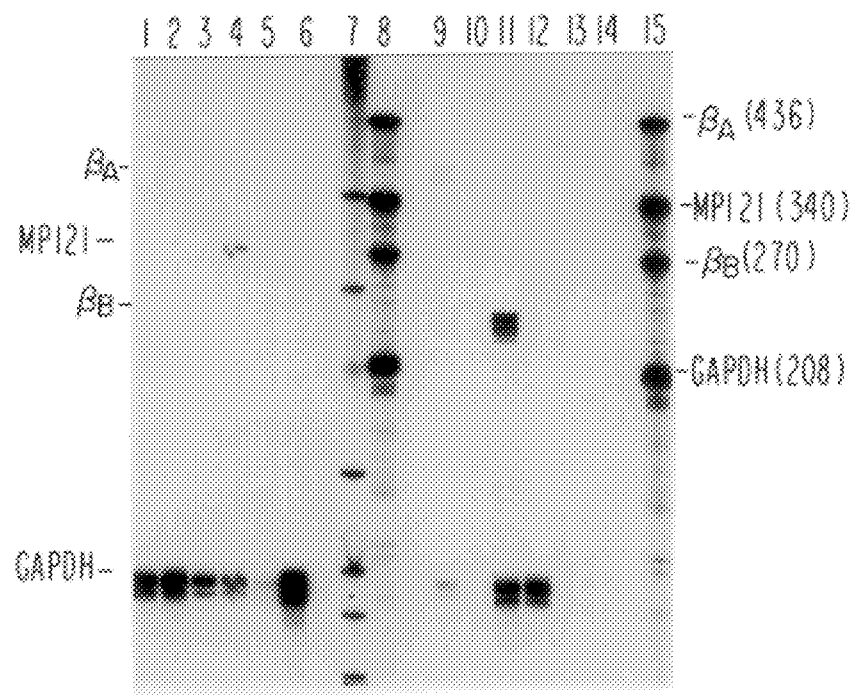

FIG. 4 shows the expression of MP121 compared to activin $β_A$ and $β_B$ in various mouse tissues.

FIG. 4 is an autoradiogram after gel analysis of a RNAse protection assay using specific probes against activin $β_A$ ($β_A$), activin $β_B$ ($β_B$), MP121 and against GAPDH for the control.

Total RNA was tested which had been isolated from various mouse tissues (1: brain, 2: heart, 3: kidney, 4: liver, 5: lung, 6: muscle, 9: ovary, 10: spleen, 11: testes), from embryonic stem cells (12: CJ7) and from yeast (lane 13) as a control. No RNA was used in lane 14 as a control. The unprotected antisense RNA probes used for the hybridization are applied in lanes 8 and 15 and the expected fragment size is indicated in brackets in the right margin. The bands of the protected fragments are labelled in the left margin. pBR322 restricted with Msp I (Biolabs #303) was used as the marker (lane 7) and end-labelled with y-$^{32}$P-ATP (Amersham).

FIG. 5 shows a positive influence on the survival of dopaminergic neurones by treatment with partially purified MP121.

This figure shows the number of TH-immunoreactive dopaminergic neurones surviving after isolation from the mesencephalon of rat embryos (E14) after 8 days culture. The effect of 20 ng/ml partially purified MP121 was tested compared to the equivalent amount of partially purified control supernatant (wt) as well as untreated neurones (control: medium containing 0.3% acetonitrile). The mean±SEM from a triple determination is shown.

Within the scope of the present invention the term "mature protein" also encompasses functional partial regions of the complete protein which exhibit essentially the same biological activity and preferably those partial regions which include at least the region of the seven cysteines that are conserved in the TGF-β family. In this case it is in particular possible that the N-terminus of the mature protein is slightly modified i.e. deviates from the sequences shown in SEQ ID NO.2 and 4. In this connection additional amino acids, which do not influence the functionality of the protein, may be present or amino acids may be absent provided that in this case the functionality is also not impaired. However, it is preferred that the human protein and the mouse protein contain all amino acids starting with amino acid 237 of the amino acid sequence shown in SEQ ID NO.2. It is already known from other family members of the TGF-β family that the attachment of additional amino acids to the N-terminus of the mature protein does not influence the activity wherein inter alia 6 additional histidines were attached to the N-terminus.

Therefore the present invention encompasses the part coding for the mature protein in accordance with the above-mentioned definition and if necessary, further functional parts of the nucleotide sequence shown in SEQ ID NO. 1 as well as sequences that correspond to this sequence within the scope of the degeneracy of the genetic code and allelic derivatives of such sequences. Furthermore the present invention also encompasses DNA sequences which code for a protein of the TGF-β family which were obtained from other mammals and which have a sequence that deviates slightly due to their origin but which, however, code for proteins having in principle the same biological function and also sequences that differ only slightly. Such sequences correspond to one another to a very large extent as can be seen by comparing SEQ ID NO. 1 and NO. 3.

In addition the present invention also covers sequences hybridizing with such sequences provided that such a DNA molecule at least completely contains the part coding for a mature protein of the TGF-β family (according to the above definition) and the biological activity is retained.

The term "functional part" within the sense of the present invention denotes a protein part which is capable of acting for example as a signal peptide, propeptide or mature protein moiety i.e. it fulfills at least one of the biological functions of the natural parts of MP-121.

In the case of the preferred human MP121 the region coding for the mature part of the protein preferably extends from nucleotide 836 to the stop codon which begins at nucleotide 1184 of the sequence shown in SEQ ID NO. 1. If necessary the DNA molecule can include further functional parts of the sequence shown in SEQ ID NO. 1 namely the nucleotide sequences coding for the signal or/and propeptide part. It is particularly preferred that the DNA molecule comprises the sequence for the signal and propeptide part and the mature protein part i.e. nucleotides 128 to 1184 of the sequence shown in SEQ ID NO. 1. In the case of the preferred mouse MP121 the region coding for the mature part of the protein preferably extends from nucleotide 839 to the stop codon starting at position 1187 of the sequence shown in SEQ ID NO.3. If desired the DNA molecule can also include further functional parts of the sequence shown in SEQ ID NO.3 i.e. if desired nucleotide sequences coding for the signal or/and propeptide part.

On the other hand the DNA molecules can also include functional signal or/and propeptide parts of other proteins e.g. of proteins with the cystine knot motif (Cell, vol. 73

(1993), p. 421–424) and in particular of other proteins of the TGF-β family e.g. the above-mentioned activin/inhibin or BMP proteins especially also MP52 (see PCT/EP94/02630) in addition to the part coding for the mature protein. The respective nucleotide sequences can be found in the aforementioned references to the disclosure of which reference is herewith made. In this case it is important that the correct reading frame for the mature protein is preserved. Depending in which host cells expression takes place, the presence of another signal sequence or/and of another propeptide part may positively influence the expression. The exchange of propeptide parts by corresponding parts of other proteins is described for example in Mol. Endocrinol. 5 (1991), 149–155 and Proc. Natl. Acad. Sci. USA 90 (1993), 2905–2909.

Although the allelic, degenerated and hybridizing sequences and sequences derived from other vertebrates which are covered by the present invention have structural differences due to slight changes in the nucleotide or/and amino acid sequence, proteins which are coded by such sequences still essentially have the same useful properties which enable them to be used in essentially the same medical fields of application.

According to the present invention the term "hybridization" denotes the usual hybridization conditions, preferably conditions with a salt concentration of 6×SSC at 62° to 66° C. followed by a one hour wash with 0.6×SSC, 0.1% SDS at 62° to 66° C.

Preferred embodiments of the present invention are DNA sequences as defined above which are obtainable from vertebrates, preferably mammals such as pigs, cows and rodents such as rats or mice and in particular from primates such as humans or which are copied from corresponding sequences.

A particularly preferred embodiment of the present invention are the sequences shown in SEQ ID NO. 1 and 3 and denoted human or mouse MIP-121 sequences. The transcripts of MP-121 were obtained from liver tissue and code for a protein which shows a considerable amino acid homology to the mature part of the inhibin/activin-like proteins (see FIG. 1). The protein sequences of human α-inhibin, inhibin $β_A$ (activin $β_A$) and inhibin $β^B$ (activin $β_B$) are described by Mason et al. (Biochem. Biophys. Res. Comm. 135, 957–964 (1986)). Some typical sequence homologies which are specific for known inhibin sequences were also found in the propeptide part of MP-121 while other parts of the propeptide of MP-121 show considerable differences to inhibin propeptides.

However previous findings show that there are differences between the pattern of expression of MP121 and that of the activins. While activins are mainly expressed in the gonads (activin $β_A$ in ovaries and activin $β_B$ in testes and ovaries), MP121 is mainly expressed in the liver. However up to now the sensitivity of the experiments has not been sufficient to also detect a slight expression. Thus in the case of activins it has for example been described in the literature that expression can also be detected outside the gonads in various rat tissues in adult animals (Meunier et al., Proc. Natl. Acad. Sci. USA 85, 247–252 (1988)) as well as during embryonic development (Roberts et al., Endocrinology 128, 3122–3129 (1991)). Therefore it is also possible that expression of MP121 in other tissues may yet be detected.

In addition the present invention concerns a vector which contains at least one copy of a DNA molecule according to the invention. In such a vector the DNA sequence according to the invention is preferably linked operatively with an expression control sequence. Such vectors are suitable for producing TGF-β-like proteins in stably or transiently-transformed cells. Various animal, plant, fungal and bacterial systems can be used for the transformation and the subsequent culture. The vectors according to the invention preferably contain sequences necessary for replication in the host cell and they are autonomously replicable. In addition the use of vectors is preferred which contain selectable marker genes by which means the transformation of a host cell can be detected.

Furthermore the invention concerns a host cell which is transformed with a DNA according to the invention or with a vector according to the invention. Examples of suitable host cells include various eukaryotic and prokaryotic cells such as *E. coli*, insect cells, plant cells, mammalian cells and fungi such as yeast.

In addition the invention concerns a protein of the TGF-β family which is coded by a DNA sequence according to claim 1. The protein according to the invention preferably has the amino acid sequence shown in SEQ ID NO. 2 or in SEQ ID NO.4 or if desired functional parts thereof (as defined above) and exhibits biological properties such as tissue-inductive properties which may be relevant for a therapeutic application. The above-mentioned features of the protein can vary depending on the formation of homodimers or heterodimers with other proteins having the "cystine knot motif" and in particular TGF-β proteins. Such structures may also prove to be suitable for clinical applications and thus are also a subject matter of the present invention. Preferred heterodimers include heterodimers composed of a monomer of the protein according to the invention and monomers of the α, $β_A$ or $β_B$ inhibin chains. The properties resulting from heterodimer formation can be shifted more towards the properties of activin or inhibins. If for example a heterodimer is formed with inhibin α proteins or with other inhibin β proteins, then it is assumed that the MP-121/inhibin (α chain) or MP 121/activin ($β_A$ or $β_B$ chain) heterodimer can inhibit or activate the formation of follicle-stimulating hormone (FSH). MP-121/activin heterodimers may also for example influence mesoderm development. Furthermore it is expected that heterodimeric forms with a member of the BMP group of TGF-β proteins lead to an amplification of BMP-like activities such as for example the ability to induce or promote bone formation, formation of cartilage or formation of connective tissue.

The invention therefore also concerns heterodimeric proteins of a protein of the TFG-β family according to the invention which is coded by a DNA sequence as claimed in claim 1 containing a monomer of a protein with the "cystine knot motif" preferably of another member of the TGF-β family. Similar heterodimeric proteins are described in WO93/09229, EP 0 626 451 A2 and J. Biol. Chem. 265 (1990), 13198–13205.

In addition the invention concerns chimeric proteins which have functional derivatives or parts of a protein coded by a DNA sequence according to the invention preferably as shown in SEQ ID NO.2 or SEQ ID NO.4, in particular functional parts of the mature protein and additionally parts of another protein. In this case the other protein can also be a protein with a "cystine knot motif" which is preferably also a member of the TGF-β family such as e.g. especially MP-52 (PCT/EP94/02630). However, parts of a complete different protein can also be present e.g. receptor-binding domains of proteins which lend the initial MP-121 protein another specificity.

The biological properties of the proteins according to the invention, preferably MP-121, can be determined for example in assays according to Wrana et al., (Cell 71, 1003–1014 (1992)), Ling et al. (Proc. Natl. Acad. of Science, 82, 7217–7221 (1985)), Takuwa et al. (Am. J. Physiol. 257, E797–E803 (1989)), Fann and Patterson (Proc. Natl. Acad. of Science, 91, 43–47 (1994)), Broxmeyer et al. (Proc. Natl. Acad. of Science, 85, 9052–9056 (1988)), Green et al. (Cell, 71, 731–739 (1992)) or Partridge et al. (Endocrinology, 108, 213–219 (1981)) or Krieglstein et al. (EMBO J. 14, 736–742 (1995)).

Activin A and TGF-β 1, TGF-β 2 and TGF-β 3 have been described to have effects on dopaminergic neurones which promote survival in vitro (Krieglstein et al., EMBO J. 14, 736–742 (1995) and Krieglstein et al., Neuroscience 63, 1189–1196 (1994)). In the case of partially purified MP121 it could be shown that the survival of dopaminergic neurones in a 8-day culture is promoted to a greater extent than by the influence of the control supernatant (FIG. 5).

The present invention in addition concerns a process for the production of a protein of the TGF-β family which is characterized in that a host cell transformed with a DNA according to the invention or with a vector according to the invention is cultured and the TGF-β protein is isolated from the cell or/and the culture supernatant. Such a process comprises culturing the transformed host cell in a suitable culture medium and purifying the TGF-β-like protein formed. In this way the process enables the production of an adequate amount of the desired protein for use in medical treatment or in applications using cell culture techniques in which growth factors are needed. The host cell can be a bacterium such as Bacillus or E. coli, a fungi such as yeast, a plant cell such as tobacco, potato or arabidopsis or an animal cell, especially a vertebrate animal cell line such as Mo, Cos or CHO cell lines or an insect cell line. When producing in bacteria it is possible that the protein according to the invention is produced in the form of inclusion bodies. These inclusion bodies are then renatured according to known methods and the protein is then obtained in an active form (see e.g. Jaenicke, R. and Rudolph, R., Protein Structure, ed. Creighton, T. E., IRL Press, chapter 9). For the production of heterodimeric proteins with other members of the TGF-β family, both protein monomers are expressed either in the same cell or separate in the course of which a common renaturation seems suitable with formation of inclusion bodies. Viral systems such as e.g. the Baculoviral system or the Vaccina viral system are in particular suitable when coexpressing in the same cell. The production of heterodimeric proteins is in principle known to a person skilled in the are and is described for example in WO93/09229 and EP 0 626 451 A2.

The production of chimeric proteins containing other protein parts requires a corresponding change at the DNA level which is familiar to a person skilled in the art and can be carried out by him (EMBO J. 10 (1991), 2105–2110; Cell 69 (1992), 329–341; J. Neurosci. 39 (1994), 195–210).

Yet another subject matter of the present invention is the provision of pharmaceutical compositions which contain a pharmaceutically effective amount of a TGF-β-like protein according to the invention as the active substance. If desired, such a composition comprises a pharmaceutically acceptable carrier or auxiliary substance, diluent or filling agent. Such a pharmaceutical composition can be used alone or in combination with other active substances for example other proteins of the TGF-β family or growth factors such as EGF (epidermal growth factor) or PDGF (platelet derived growth factor) in wound healing and tissue regeneration. Furthermore such a pharmaceutical composition can be used for the prevention of diseases.

Further subject matters are pharmaceutical compositions which contain heterodimeric proteins or/and chimeric proteins according to the invention.

The pharmaceutical composition according to the invention is preferably used for the treatment and prevention of damage to bones, cartilage, connective tissue, skin, mucous membranes, endothelium, epithelium, neurones, kidneys or teeth, for application in dental implants, for application in wound healing or tissue regeneration processes, as a morphogen for use in the induction of liver tissue growth, induction of the proliferation of precursor cells or bone marrow cells, for the maintenance of a state of differentiation and for the treatment of disturbances in fertility or for contraception.

A further possible clinical application of the TGF-β-like protein according to the invention is the use as a suppressor of immunoreactions in order to avoid rejection of organ transplants or use in connection with angiogenesis. Furthermore the protein according to the invention can be used to increase fertility or in contraception. The pharmaceutical composition according to the invention can also be used prophylactically or in cosmetic surgery. Furthermore the application of the composition is not limited to humans but can also include animals in particular pets and domestic animals.

Thus the part of the other protein or other monomer can be used to vary the scope of applications and specificity of heterodimeric proteins and chimeric proteins as desired.

In general diseases which are associated with the expression of MP-121 can be treated using the proteins according to the invention either by increasing the amount or activity of MP-121 which is present or by suppressing the MP-121 activity. Thus the invention also concerns the production of antisense nucleic acids and ribozymes which inhibit the translation of MP-121. This inhibition can either be achieved by masking the mRNA with an antisense nucleic acid or by cleavage with a ribozyme.

The production of antisense nucleic acids is known (Weintraub, H. M., Scientific American 262: 40 (1990)). The antisense nucleic acids hybridize with the respective mRNA and form a double-stranded molecule which can then no longer be translated. The use of antisense nucleic acid is for example known from Marcus-Sekura, C. J., Anal. Biochem. 172 (1988), p. 289–295.

Ribozymes are RNA molecules which are able to specifically cleave other single-stranded RNA molecules similar to DNA restriction endonucleases. The production of ribozymes is described in Cech, J. Amer. Med. Assn. 260 (1988), p. 3030.

In this connection it is also possible according to the invention to transfect suitable vectors containing the DNA sequence according to the invention in vitro or in vivo into patient cells or to transfect the vectors in vitro into cells and then to implant these in a patient.

MP-121 antisense polynucleotides can also be introduced into cells which exhibit an undesired expression of MP-121.

The MP-121 activity can also be suppressed by binding molecules to the MP-121 receptors which, in contrast to MP-121, do not trigger further transmission of a signal.

Thus within the scope of the invention the receptors for MP-121 on cells are also of interest. In order to find receptors, firstly various cell lines can be tested for their binding properties with respect to radioactively-labelled MP-121 ($^{125}$I-MP-121) with subsequent cross-linking. A cDNA library can subsequently be established in an expression vector (obtainable from InVitrogen) from cells which bind MP-121. Cells which have been transfected with receptor cDNA can then be selected by the binding of radioactively-labelled MP-121. These are methods known to a person skilled in the art and have for example been used to isolate activin (Mathews, L. S. & Vale, W. W., Cell 65 (1991), 973–982) and TGF-β type II receptors (Lin, H. Y. et al., Cell 68 (1992), 775–785). In analogy to known activin receptors, the MP-121 receptor is also presumably a receptor complex which belongs to this family so that further methods known to a person skilled in the art, such as e.g. PCR with degenerate oligonucleotides, can be used to find parts of the heteromeric complex. This method has also been used for example with the activin and TGF-β type I receptors (Tsuchida et al., Proc. Natl. Acad. Sci. USA 90 (1993), 11242–11246; Attisano et al., Cell 75 (1993), 671–680; Franzén et al., Cell 75 (1993), 681–692).

Finally the present invention concerns an antibody which can bind specifically to the proteins according to the invention or such an antibody fragment (e.g. Fab or Fab'). Processes for the production of such a specific antibody or antibody fragment are part of the general knowledge of an average person skilled in the art. Such an antibody is preferably a monoclonal antibody. Such antibodies or antibody fragments can also be suitable for diagnostic methods.

In addition it is intended to illustrate the invention by the following examples.

EXAMPLE 1

Isolation of MP-121

1.1 Total RNA was isolated from human liver tissue (40 year old man) according to the method of Chirgwin et al. (Biochemistry, 18, 5294–5299 (1979)). Poly (A+)-RNA was separated from the total RNA by oligo (dT) chromatography according to the manufacturer's instructions (Stratagene poly (A) Quick columns).

1.2 For the reverse transcription reaction 1 to 2.5 µg poly (A+) RNA was heated for 5 minutes to 65° C. and quickly cooled on ice. The reaction mixture contained 27 U RNA-Guard (Pharmacia), 2.5 µg oligo (dT)$_{12-18}$ (Pharmacia), 5×buffer (250 mmol/l Tris/HCl pH 8.5, 50 mmol/l MgCl$_2$, 50 mmol/l DTT, 5 mmol/l of each dNTP, 600 mmol/l KCl) and 20 U AMV reverse transcriptase (Boehringer Mannheim) per µg poly (A+) RNA. The reaction mixture (25 µl) was incubated for 2 hours at 42° C. The cDNA pool was stored at −20° C.

1.3 The deoxynucleotide primers OD and OID shown in FIG. 2 were prepared on an automatic DNA synthesizer (Biosearch). Purification was carried out by means of denaturing polyacrylamide gel electrophoresis and isolating the main bands from the gel by isotachophoresis. The oligonucleotides were designed by comparing nucleic acid sequences of known members of the TGF-β family and selecting regions with high conservation. A comparison of this region is shown in FIG. 2. In order to facilitate cloning, both oligonucleotides contained Eco RI cleavage sites and OD additionally contained a Nco I restriction cleavage site at its 5' terminus.

1.4 In the PCR reaction cDNA corresponding to 20 ng poly (A+) RNA were used as starting material (see 1.2) The reaction was carried out in a volume of 50 µl and contained 1×PCR buffer (16.6 mmol/l (NH$_4$)$_2$SO$_4$, 67 mmol/l Tris/HCl pH 8.8, 2 mmol/l MgCl$_2$, 6.7 µmol/l EDTA, 10 mol/l β-mercaptoethanol, 170 µg/ml bovine serum albumin (Gibco), 200 µmol/l of each dNTP (Pharmacia), 30 pmol of each oligonucleotide (OD and OID) and 1.5 U Taq polymerase (AmpliTaq, Perkin Elmer Cetus). The reaction mixture was overlayed with paraffin and 40 PCR cycles were carried out. The products of the PCR reaction were purified by means of phenol/chloroform extraction and concentrated by ethanol precipitation.

1.5 Half of the PCR reaction products was cleaved with the restriction enzymes SphI (Pharmacia) and AlwNI (Biolabs) according to the manufacturer's instructions. The other half was cleaved in a series of reactions using Ava I (BRL), AlwN I (Biolabs) and Tfi I (Biolabs). The restrictions were carried out in 100 µl using 8 U enzyme for 2 to 12 hours at 37° C. (apart from Tfi I at 65° C.)

1.6 The products of the restriction cleavage were fractionated by means of agarose gel electrophoresis. After staining with ethidium bromide, uncleaved amplification products were cut out of the gel and isolated by phenol extraction. The DNA obtained was subsequently purified twice by phenol/chloroform extraction.

1.7 A quarter or a fifth of the isolated DNA was reamplified after ethanol precipitation using the same conditions as for the primary amplification except that the number of cycles was reduced to 13. The reamplification products were purified, cleaved with the same enzymes as above and uncleaved products were isolated from the agarose gels as elucidated above for the amplification products. The reamplification step was repeated.

1.8 After the last isolation from the gel, the amplification products were cleaved by 4 U Eco RI (Pharmacia) under the conditions recommended by the manufacturer. A quarter of the restriction mixture was ligated into the vector pBluescript SK+ (Stratagene) which had been cleaved with Eco RI. After ligation, 24 clones of each enzyme combination were analyzed further by sequencing. There were no new sequences in the mixture which had been cleaved with AlwN I and Sph I, it contained only BMP6 and inhibin βA sequences. 19 identical new sequences, named MP-121, were found in the mixtures cleaved with Ava I, AlwN I and Tfi I. These plasmids were named pSK-MP-121 (OD/OID). One sequence differed by two nucleotides from this sequence that was otherwise found. Ligation and transformation in E. coli was carried out as described in Sambrook et al., Molecular Cloning: A Laboratory Manual (1989).

The clone was extended to the 3' end of the cDNA according to the method described in detail by Frohmann (published by Perkin-Elmer Corp., Amplifications, 5, 11–15 (1990)). The same liver mRNA which had been used to isolate the first MP-121 fragment was reversely transcribed as described above using oligo dT (16mer) linked to the adapter primer (AGAATTCGCATGCCATGGTCGACGAAGC -T$_{16}$) SEQ ID NO:7. The amplification was carried out using the adapter primer (AGAATTCGCATGCCATGGTCGACG) SEQ ID NO:8 and an internal primer (GGCTACGCCATGAACTTCTGCATA) SEQ ID NO:9 prepared from the MP-121 sequence. The amplification products were prepared using a further internal primer (ACATAGCAGGCATGCCTGGTATTG) SEQ ID NO:10 prepared from the MP-121 sequence and with the adapter primer. After restriction with Sph I the reamplification products were cloned into the vector pT7/T3 U19 (Pharmacia) which had been cleaved in the same way and sequenced. The clones were characterized by their sequence overlap with the already known part of the MP-121 sequence. One clone, named p121Lt 3' MP13, was used to isolate a Nco I (made blunt using T4 polymerase)/Sph I fragment. This fragment was cloned into one of the above-mentioned pSK-MP-121 (OD/OID) vectors whose OD primer sequence was orientated towards the T7 primer of the pSK multiple cloning site. For this the vector was cleaved with SphI and SmaI. The construct was named pMP-121DFus6. It comprises the MP-121 sequence from position 922 to 1360 as shown in SEQ ID NO. 1.

1.9 A Dde I fragment of pMP-121DFus6, which extends from position 931 to 1304in SEQ ID NO. 1, was used to screen a human liver cDNA library (Clontech, #HL3006b, lot 36223) as described in detail by Ausubel et al., (Current Protocols in Molecular Biology, published by Greene Publishing Associates and Wiley-Interscience (1989)). 24 mixed plaques were picked from $8.1 \times 10^5$ phages and separated. From this 10 clones which yielded a positive signal using primer LO2 (ACATAGCAGGCATGCCTGGTATTG) SEQ ID NO:11 and LOI1 (CTGCAGCTGTGTTGGCCTTGAGA) SEQ ID NO:12 from the Dde I fragment were selected and separated. The cDNA was isolated from the phages by means of an EcoRI restriction and cloned into the pBluescript SK vector which had also been cleaved with EcoRI.

Sequencing of one of the resulting plasmids SK121L9.1 showed that the start codon begins at position 128 of SEQ ID NO. 1 since three stop codons are positioned in-frame in front of this start codon at positions 62, 77 and 92. Mature MP-121 starts at position 836 of SEQ ID NO. 1 assuming sequence analogy to other TGF-β proteins which corresponds to amino acid 237 in SEQ NO.2. The stop codon begins at position 1184 of SEQ ID NO. 1.

Plasmid SK121L9.1 was deposited at the DSM on the 26.04.1994 under the deposit number 9177.

1.10 Isolation of the MP121 cDNA and genomic DNA from the mouse:

The sequence information from the human MP121 sequence was used to isolate the MP121 sequence from the mouse. The methods used for this are all known to a person skilled in the art and are described for example in Current Protocols in Molecular Biology (Ausubel et al., Greene Publishing Associates and Wiley-Interscience, Wiley & Sons, 1987–1995) or in Molecular Cloning (Sambrook et al., second edition, Cold Spring Harbour Laboratory Press 1989). Firstly the primers ACGAATTCCQACGAGGCATCGACTGC SEQ ID NO:13 and GCGTCGACTAC-CATGTCAGGTATGTC SEQ ID NO:14 were synthesized from the human MP121 sequence with additional restriction cleavage sites at the 5' end (EcoR I or Sal I). These primers were used for amplification on genomic mouse DNA. The 0.35 kb fragment which results was subcloned in the Bluescipt vector (Stratagene) and used as a radioactive probe. A λ bank with genomic mouse DNA as well as a bank with cDNA was screened according to standard methods. The cDNA was synthesized from RNA, which had been isolated from mouse liver, and cloned into λgt10 often being provided with EcoR I/Not I linkers.

MP121 clones were isolated from the genomic as well as from the cDNA bank. A cDNA containing the complete coding sequence was subcloned into the EcoR I cleavage site of the Bluescript vector SK (Stratagene) and the resulting plasmid SKMP121 mouse was deposited on the 10.05.1995 at the DSM (DSM 9964). Complete sequencing resulted in the sequence shown in SEQ ID NO.3. The start codon begins at position 131 in SEQ ID NO.3 and ends at the stop codon starting at position 1187. The protein derived from the sequence is shown in SEQ ID NO.4. Subcloning and analyzing clones containing MP121 from the genomic bank showed that the MP121 sequence contains an intron in the propeptide part of ca. 5.5 kb. This intron is located between positions 446 and 447 in SEQ ID NO.3. The exon/intron junctions are shown in SEQ ID NO.5.

EXAMPLE 2

Expression of MP-121

It is possible to express MP-121 in eukaryotic as well as in prokaryotic systems.

Only the mature part of MP-121 was used for expression in prokaryotes. After purification the mature MP-121 protein expressed in E. coli as a monomer can then be folded back to form a dimer. In order to simplify purification of MP-121, an additional 6 histidines can be attached to the N-terminus of the mature protein which facilitate purification of the protein by binding to nickel-chelate columns.

As an example the mature part of human MP-121 (amino acid 237 to 352 in SEQ ID NO.2) with an additional 13 amino acids, including 6 histidines at the N-terminus, (MHHHHHHKLEFAM SEQ ID NO:15) was expressed in the prokaroytic vector pBP4. This vector is a pBR322 derivative having tetracyclin resistance which in addition contains the T7 promoter from the pBluescript II SK plasmid (Stratagene). Furthermore the vector contains a ribosomal binding site following the T7 promoter and a start codon followed by 6 codons for histidine. A terminator (TØ) follows after several single restriction cleavage sites such as Eco RI, Xho I, Sma I and Apa I for the insertion of inserts as well as stop codons in all three reading frames. In order to obtain the cDNA for the mature part of MP-121, PCR was carried out on the plasmid SK121L9.1 (DSM depositary number: 9177) using the two oligonucleotides GAAT-TCGCCATGGGCATCGACTGCCAAGGAGG SEQ ID NO:16 and CCGCTCGAGAAGCTTCAACTGCACCCA-CAGGC SEQ ID NO:17. Both oligo-nucleotides contain additional restriction cleavage sites at their ends (Eco RI and Nco I or Xho I and Hind III). In an intermediate step the resulting 377 bp fragment was cloned with blunt ends into the pBluescript II SK vector (Stratagene) that had been cleaved with Eco RV. One clone in the orientation of the 5' end of MP-121 towards the T7 promoter was cleaved with Eco RI and the resulting insert (0.38 kb) was cloned into the pBP4 vector that had also been cleaved with Eco RI. The correct orientation of the insert in the resulting plasmid pBP4MP-121His was established by restriction analysis and sequencing. The plasmid pBP4MP-121His was deposited on the 30.1.1995 at the DSM (depositary number: 9704). The expression of MP-121 protein can be achieved by simultaneously providing T7 RNA polymerase. T7 RNA polymerase can be provided by various methods such as e.g. by a second plasmid with a gene for T7 RNA polymerase or by infection with phages which code for T7 RNA polymerase or also by special bacterial strains which have integrated the gene for T7 RNA polymerase. The mature MP-121 protein with a His-tag (MP-121His) is produced in inclusion bodies by using the bacterial strain BL21 (DE3)pLysS (Novagen, #69451–1) and inducing the T7 RNA polymerase expression with IPTG according to the manufacturer's instructions. In SDS polyacrylamide gels (15%) the protein exhibits an apparent molecular weight of nearly 16 kD (theoretical molecular weight: 14.2 kD) as is shown representatively in the Western blot of FIG. 3. The bacteria transformed with pBP4 as controls do not show any staining of specific bands. Due to the His-tag this protein can be purified on nickel-chelating agent columns as described for example by Hochuli et al., (BIO/Technology Vol. 6, 1321–1325 (1988)).

An additional purification is possible by means of reversed phase HPLC. A reversed phase column (Nucleosil 300–7C4 from Macherey-Nagel, Type 715023) was used with a flow-rate of 2 ml/min and an acetonitrile gradient in 0.1% TFA of 0 to 90% within 100 minutes. MP-121His elutes under these conditions after ca. 40% acetonitrile.

In each case the determination whether it is MP-121 protein was carried out by means of Western blot analysis using MP-121-specific antibodies. Polyclonal antibodies against MP-121 were produced in chicken as well as in rabbits. In order to obtain the antigen for the immunization, a part of the mature part of MP-121 (amino acid 260 to 352 in SEQ ID NO.2) was fused with the first 98 amino acids of the polymerase of the MS2 bacteriophage and expressed in E. coli. After isolating the inclusion bodies, the fusion protein (MS2-MP-121) was separated on polyacrylamide gels and isolated for the immunization after staining with copper by means of electro-elution (Tessmer, U. & Dernick, R., IBL (1990) 8–13). It is possible to specifically detect the expression of MP-121 using antibodies from chicken as well as from rabbits. Chicken antibodies were used for the schematic Western blot in FIG. 3 which had been purified further by means of PEG precipitation (Thalley B. S. and Carroll, S. B., BIO/Technology Vol. 8, 934–938 (1990)) and by means of membrane-bound antigen (fusion protein (MS2-MP-121)) (18.17 in Sambrook et al., Molecular Cloning, second edition, Cold Spring Harbor Laboratory Press 1989). Anti-chicken IgG coupled to alkaline phosphatase (Sigma A9171) was used as the second antibody. The detection was carried out according to the manufacturer's instructions using the Tropix Western-Light Protein Detection Kit (Serva #WL10RC).

In order to obtain biologically active material, the purified monomeric MP-121 expressed in E. coli can be folded back to form a dimeric MP-121. This can be carried out according to the methods for example described by Jaenicke, R. & Rudolph, R. (Protein structure, ed. Creighton, T. E., IRL Press, chapter 9).

The Vaccinia viral expression system was used for expression in eukaryotic cells as it is described in detail and in a form which can easily be repeated by a person skilled in the art in Current Protocols in Molecular Biology (Ausubel et al., Greene Publishing Associates and Wiley-Interscience, Wily & Sons) abbreaviated in the following as CP, in chapter 16 unit 16.15–16.18. The system is based on the fact that foreign DNA can be integrated by homologous recombination into the genome of the Vaccinia virus using certain vectors. For this purpose the vector used contains the TK (thymidine kinase) gene from the Vaccinia genome. In order to enable selection for recombinant viruses, the vector additionally contains the E. coli xanthine-guanine-phosphoribosyl transferase gene (gpt) (Falkner, F. G. & Moss, B., J. of Virol. 62 (1988), 1849–1854). The cDNA with the complete region coding for MP-121 was cloned into this vector.

PCR reactions and intermediate cloning was necessary in order to shorten the 5' and 3' untranslated regions of the initial plasmid SK121L9.1 (DSM, depositary number: 9177) and to insert single restriction cleavage sites at the ends. All PCR reactions were carried out using the plasmid SK121L9.1 (DSM despositary number: 9177). In order to shorten the 5' untranslated end, the primer CCCGGATCCGCTAGCACCATGACCTCCTCATTGCTTCTG SEQ ID NO:18 with an inserted Bam HI and NheI restriction cleavage site was used in a PCR with an internal primer (CCCTGTTGTCCTCTAGAAGTG) SEQ ID NO:19. In an intermediate step the fragment obtained was cloned into Bluescript SK (Stratagene), sequenced and checked for concurrence with the sequence shown in SEQ ID NO.1. The Sph I/Eco RI fragment (0.22 kb) from the plasmid pBP4MP-121His was used to shorten the 3' untranslated end.

Both end fragments of MP-121 were linked to the missing middle DNA sequence from the plasmid SK121L9.1 (DSM depositary number: 9177) by means of internal restriction cleavage sites (Xba I and Sph I) according to standard methods (Sambrook et al. Molecular Cloning, second edition, Cold Spring Harbor Laboratory Press 1989). The shortened cDNA obtained in this way having the complete reading frame for MP-121 (nucleotide 128 to nucleotide 1184 in SEQ ID NO.1) could be cloned into the vector pBPl which had also been cleaved by using the restriction cuts Bam HI and Eco RI. The resulting plasmid pBP1MP-121 was deposited on 12.1.95 at the DSM (depositary number: 9665).

The plasmid pBP1MP-121 was used for the production of recombinant Vaccinia viruses. For this 143B cells (HuTk-, ATCC CRL 8303) which were 80% confluent were infected with Vaccinia wild-type virus (1 virus per 10 cells) in 1 ml PBS in 35 mm culture plates for 30 minutes at room temperature while shaking occasionally. After aspirating the supernatant and adding 2 ml culture medium (MEM, Gibco BRL #041–01095 containing 1:500 diluted penicillin and streptomycin Gibco BRL #043-05140), they were incubated for 2 hours at 37° C. Subsequently the medium was removed and these cells were transformed for ca. 15 hours at 37° C. using 100 ng pBP1MP-121, 2 µg carrier DNA (calf thymus, treated with ultrasound, Boehringer Mannheim #104175) and 10 µl Lipofectin (Gibco BRL #18292-011) in 1 ml MEM. After addition of 1 ml MEM containing 20% FCS (Sigma #F-7524) they were incubated for a further 24 hours at 37° C. and subsequently the lysed cells were frozen.

Gpt selection for xanthine-guanine-phosphoribosyl transferase and isolation and amplification of individual recombinant viruses was essentially carried out as described in unit 16.17 of CP with the difference that RK13 cells (ATCC CCL 37) were used.

Integration of the MP-121 cDNA into the viral genome was confirmed by dot blot analysis (CP unit 16.18). A recombinant virus from the transfection with pBPMP-121 and the wild-type virus were used for expression analyses in cell lines 143B (HuTk-, ATCC CRL 8303, human) and NIH-3T3 (DSM ACC 59, Swiss mouse embryo). The cells were cultured according to the distributor's instructions. Confluent cells were infected for 30 minutes at 37° C. with the three-fold number of viruses and subsequently the respective culture medium containing 10% FCS and penicillin/streptomycin (1:500, Gibco BRL #043-05140) was added. The medium was removed after 6 hours at 37° C., the cells were washed twice with e.g. HBSS (Gibco BRL #14180-046) and production medium (MEM for HuTk- or DMEM containing 4.5 g/l glucose and NEAA (Gibco BRL #11140-035) for NIH-3T3 each of which contained aprotinin (Fluka #10820, 50 U/ml) and penicillin/streptomycin) without FCS. After a production period of 20 to 22 hours, the cell supernatant was collected. The expression was analysed by means of Western blots according to standard methods (CP unit 10.8). For this the proteins from 1 to 3 ml cell culture supernatant were precipitated by addition of an equivalent volume of acetone and incubating for at least one hour on ice and centrifuged. After resuspending the pellets in application buffer (7M urea, 1% SDS, 7 mM sodium dihydrogen phosphate, 0.01% bromophenol blue and 1% β-mercaptoethanol if desired) they were separated in 15% polyacrylamide gels. A pre-stained protein molecular weight standard (Gibco BRL #6041-020) was used as marker proteins. Transfer onto a PVDF membrane (Immobilon #IPVH00010) and blocking the membrane was carried out according to standard methods.

Figure 3:
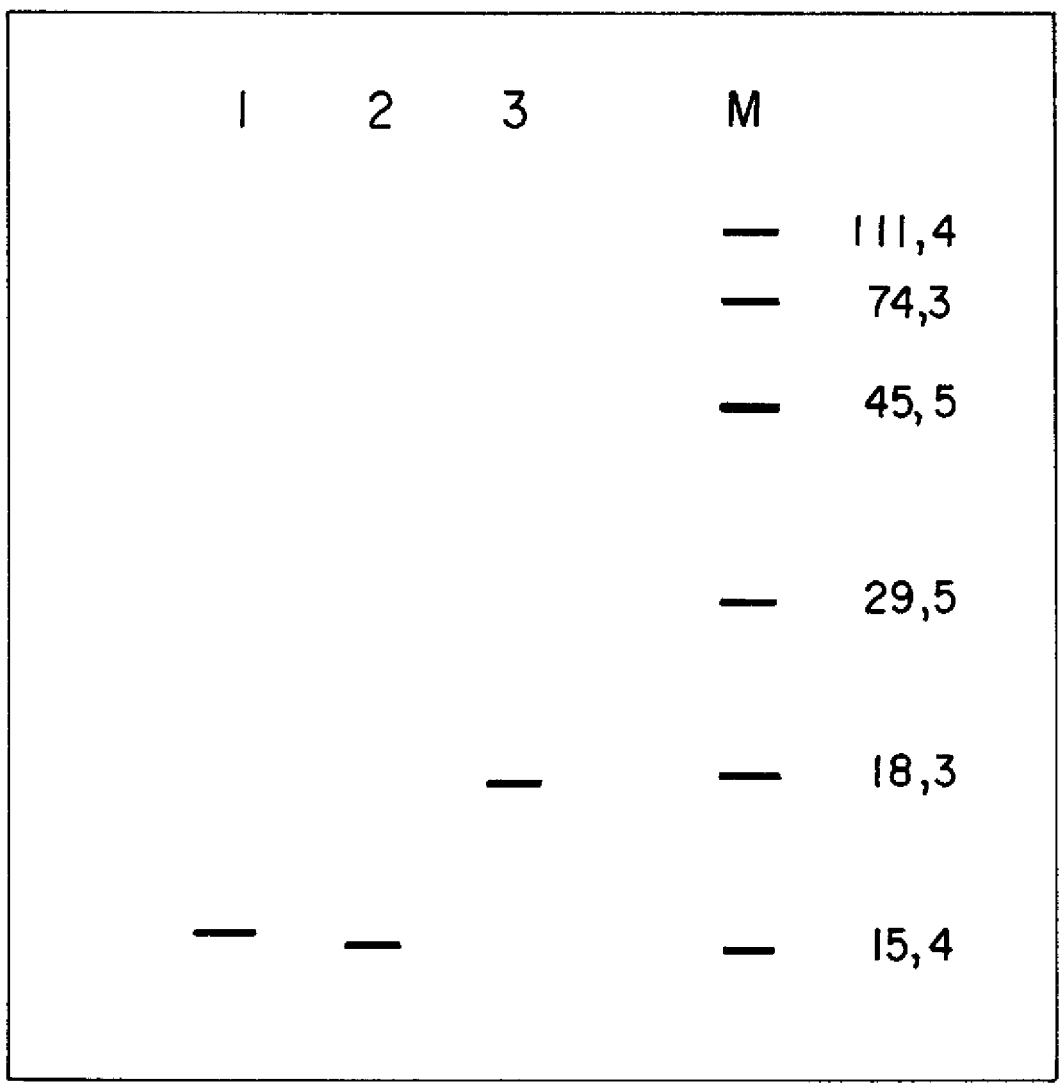
FIG. 3 shows a diagram of a Western blot using chicken antibodies against human MP121.

A representative schematic diagram of the results of the Western blot in FIG. 3 shows that MP-121-specific bands occur in the recombinant viruses. The expression of MP-121 in NIH-3T3 cells leads to a secreted protein with an apparent molecular weight in the gel of about 18 kDa under non-reducing conditions (expected theoretical molecular weight: 25 kD). Under reducing conditions the protein migrates at about 15 kDa in the gel (expected theoretical molecular weight: 12.5 kD). These results show that MP-121 is expressed as a dimeric mature protein as expected. The migration behaviour of the dimeric MP-121 protein which is only slightly slower than the monomeric MP-121 protein is probably due to its globular structure. The processing of the precursor protein to form the mature protein could also be demonstrated in HuTK cells. No bands occurred in the Western blot with cells (HuTK- or NIH-3T3) infected with wild-type viruses (without integrated foreign DNA).

When co-transfection with recombinant Vaccinia viruses that code for various members of the TGF-β family has also taken place, the Vaccinia expression system is also particularly suitable for the production of heterodimers. It is then possible to separate heterodimers from homodimers by affinity columns using specific antibodies against the individual members of the TGF-β family. In this case the a as well as βA and βB chains of inhibins are of particular interest.

EXAMPLE 3

Investigation of the Expression of MP121 in Various Mouse Tissues

Total RNA from various tissues (brain, heart, kidney, liver, lung, spleen, muscle, ovary, testes) was isolated according to standard methods from 6 week-old mice as well as from embryonic stem cells. 10 μg total RNA was used in each case in a RNAse protection assay (RPA) from Ambion (RPA II kit, #1410) according to the manufacturer's instructions. In order to obtain specific probes for activin $β_A$ and activin $β_B$, the genomic DNA from the mouse (128Sv) was amplified from the mature part of the proteins using corresponding specific primers. In order to facilitate cloning, EcoR I and/or BamH I or Hind III restriction cleavage sites were introduced respectively at the ends of the primers. In the case of activin $β_A$ the primers were derived from mRNA from rats (GenBank Accession #M37482): GGATCCGAAT-TCGGCTTGGAGTGTATGGCAAGG SEQ ID NO:20 and GGATCCGAATTCCTCTGGGACCTGGCAACTCTAG SEQ ID NO:21.

In the case of activin $β_B$ degenerate primers were derived from the human sequence (Mason et al., Molecular Endocrinology 3, 1352–1358 (1989): GAGAATTCCA(GA)CA(GA)TT(TC)TT(CT)AT SEQ ID NO:22 and GCAAGCTTT(GA)TA(TC)TC(GA)TC(GA)TC SEQ ID NO:23.

The resulting PCR fragments were subcloned into the vector pGEM-4 (Promega) and tested. The activin-specific and thus RPA-protected sequences have a fragment size of 369 bp in the case of activin $β_A$ and 254 bp in the case of activin $β_B$. In MP121 the protected fragment comprises the sequence from position 887 to position 1164 in SEQ ID NO:3. The fragments cloned into pGEM-4 were transcribed in vitro in order to produce radioactively-labelled antisense RNA probes. This was carried out according to the manufacturer's instructions (Promega, Riboprobe Gemini Systems) using 100 μM CTP and at the same time $α^{32}$P-CTP (800 Ci/mmol, Amersham). A radioactively-labelled RNA was also synthesized as a control from the plasmid pTri-GAPDH (Ambion #7431) linearized with Dde I but using 1 mM CTP. After isolating the 4 antisense RNA probes from polyacrylamide gels, these were incubated at 42° C. overnight in the same mixture with the respective tissue RNA from the mouse (10 μg total RNA per probe having $1×10^5$ cpm). It was analyzed in a denaturing gel according to standard methods with a subsequent autoradiography for 4 days.

EXAMPLE 4

Partial Purification of MP121 and Examination of the Activity of Partially Purified MP121

The MP121 protein which had been obtained by expression in the Vaccinia system (see example 2) could be partially purified by means of two columns.

In order to produce MP121 confluent NIH-3T3 cells (DSM ACC 59, Swiss mouse embryo) were infected with the same number of recombinant viruses for 30 minutes at 37° C. and subsequently the appropriate culture medium containing 10% FCS and penicillin/streptomycin was added. After 4 hours at 37° C. the medium was removed, the cells were washed twice and production medium (see example 2) without FCS was added. After 20 to 22 hours production, the cell supernatant was collected and centrifuged in order to remove the viruses (40000×g for 30 minutes at 4° C.) and filtered (0.1 μm pore size, Millec W., Millipore #SLVV25LS). The control supernatant (wt) was obtained in a comparable manner after infection by wild-type Vaccinia viruses. The expression of MP121 was checked by means of Western blot analysis and estimated to be 50–100 μg/l.

The cell culture supernatant containing MP121 (1.1 l) was admixed with the protease inhibitor PMSF (1 μM), brought to a final concentration of 1M $(NH_4)_2SO_4$, 20 mM Tris pH 8.0 and loaded onto a phenyl-Sepharose (fast flow (high sub) Pharmacia #17-0973-05) column (5 ml bed) equilibrated in buffer A (1M $(NH_4)_2SO_4$, 20 mM Tris pH 8.0). The loaded column was washed with 15 column volumes of buffer A and 10 column volumes of buffer B (20 mM Tris pH 8.0) and eluted within 50 minutes (5 ml per fraction) with a linear gradient to 100% buffer C (20 mM Tris pH 8.0, 80% ethylene glycol) at a flow rate of 1 ml/min. It was possible to check that MP121 eluted between 50 and 80% ethylene glycol by means of Western blot analysis. Aliquots of these fractions were examined using 15% polyacrylamide silver-stained gels according to the manufacturer's instructions (Silver Stain-II, Daiichi #SE140000) and the fractions containing MP121 were pooled. After purification of the control supernatant comparable fractions were also pooled after analysis in silver-stained gels.

The pooled fractions were purified further with the aid of reversed phase HPLC. For this a C8 column (Aquapore RP300, Applied Biosystems, particle size: 7 μm, pore size: 300Å) was equilibrated with buffer A (0.1% trifluoroacetic acid/water). After loading the column with the pooled fractions containing MP121 from the phenyl-Sepharose column, it was extensively washed with buffer A. The bound protein was eluted at a flow rate of 0.2 ml/min using a linear gradient of 1.5% buffer B (90% acetonitrile, 0.1% trifluoroacetic acid) per minute. Fractions of 600 μl were collected and analyzed in a Western blot as well as with silver-stained gels. Under the selected conditions MP121 protein eluted after 55% acetonitrile. The fractions containing MP121 were pooled. The same was carried out with the corresponding fractions from the purification of the control supernatant. The analysis in the silver gel showed that MP121 was still contaminated by other proteins. Further purification steps are necessary to obtain pure MP121.

Other methods known to a person skilled in the art such as gel sieve columns, ion exchange columns, affinity columns or metal chelate columns could also be used for the further purification.

It was estimated from Western blot analysis that ca. 8 µg partially purified MP121 was obtained from 1 l. The partially purified protein was stored lyophilized at −80° C.

In order to investigate the influence of MP121 on dopaminergic neurones, neurones from the mesencephalic base of 14 day-old rat embryos (E14) were isolated according to a method described by Shimoda et al. (Brain Res. 586, 319–331 (1992)). The cells were singled out and cultured as described by Krieglstein et al., (Neuscience 63, 1189–1196 (1994)). The cell density on polyornithine/laminin-coated cover glasses is 200000 cells/cm$^2$. After culture for 24 hours and subsequently every three days two-thirds of the medium (500 µl) was removed and replaced by fresh medium containing the respective additives. The lyophilized MP121 partially purified by phenyl-Sepharose and reversed phase HPLC was dissolved in 50% acetonitrile and added to the medium. The final concentration of MP121 in the medium is 20 ng/ml (the final concentration of acetonitrile is 0.3%). A comparable amount from the control supernatant (wt) which had been purified in a comparable manner, was dissolved in 50% acetonitrile and added. The medium control also contains 0.3% acetonitrile. After eight days the cultures were fixed for 10 minutes at room temperature in 4% paraformaldehyde; the cells were made permeable with acetone (10 min, −20° C.) and washed with PBS (phosphate buffered saline). After treatment with 1% H$_2$O$_2$ in PBS, washing and blocking with horse serum, they were stained immunocytochemically. Tyrosine hydroxylase (TH) is a limiting enzyme in the biosynthesis of dopamine and other catecholamines so that TH can be used as a marker for dopaminergic neurones in the present cultures (cells containing noradrenaline were not isolated). TH was detected by a 1 hour incubation at 37° C. using a mouse-monoclonal antibody against rat TH (diluted 1:200, Boehringer Mannheim) and subsequent detection using the Vectastain ABC kit (Vecto Labs). TH-positive cells were counted in an area of 0.12 cm$^2$. It can be seen from FIG. 5 that MP121 has a positive effect on the survival of dopaminergic neurones.

We claim:

1. An isolated and purified DNA molecule that codes for a protein of the TGF-β family, wherein said molecule is selected from the group consisting of:
   (a) a molecule comprising the nucleotide sequence shown in SEQ ID NO.1, or the following fragments thereof: nt 128–1183, nt 836–1183, nt 128–835, and nt 866–1180;
   (b) a molecule encoding a nucleotide sequence corresponding to a naturally occurring allelic variant of the protein coded by (a);
   (c) a molecule encoding the amino acid sequence encoded by (a) or (b); and
   (d) a sequence which differs from sequence (a) due to its origin from other mammals.

2. The DNA molecule as claimed in claim 1, further comprising a nucleic acid sequence which codes for at least a part of another protein comprising the cystine knot motif and which is arranged in such a way that after expression a fusion protein results.

3. A vector comprising at least one copy of the DNA molecule as claimed in claim 1.

4. A host cell which is transformed with the DNA as claimed in claim 1.

5. The host cell of claim 4, selected from the group consisting of a bacterium, a fungus, a plant and an animal cell.

6. Process for the production of a protein of the TGF-β family comprising culturing a host cell containing an expression vector comprising the DNA molecule of claim 1, and obtaining said protein from the cell or/and the culture supernatant.

* * * * *

UNITED STATES PATENT AND TRADEMARK OFFICE
CERTIFICATE OF CORRECTION

PATENT NO. : 5,807,713

DATED : September 15, 1998

INVENTOR(S) : Hötten et al.

It is certified that error appears in the above-identified patent and that said Letters Patent is hereby corrected as shown below:

Column 3, lines 28 and 31, delete "(1% Ô-mercaptoethanol)"

insert therefor -- (1% β-mercaptoethanol) --

Sheet 1 of 5, Fig. 1, MP121, position 21, delete "O" insert therefor -- Q --.

Sheet 1 of 5, Fig. 1, INHIB βB, position 17, delete "C"

insert therefor -- D --.

Title page,
Item [30], line 1, delete "92102324" insert therefor

-- 92 102 324.8 --.

Signed and Sealed this

Twenty-third Day of February, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
( A ) LENGTH: 2272 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

```
CAAGGAGCCA  TGCCAGCTGG  ACACACACTT  CTTCCAGGGC  CTCTGGCAGC  CAGGACAGAG      60

TTGAGACCAC  AGCTGTTGAG  ACCCTGAGCC  CTGAGTCTGT  ATTGCTCAAG  AAGGGCCTTC     120

CCCAGCAATG  ACCTCCTCAT  TGCTTCTGGC  CTTTCTCCTC  CTGGCTCCAA  CCACAGTGGC     180

CACTCCCAGA  GCTGGCGGTC  AGTGTCCAGC  ATGTGGGGGG  CCCACCTTGG  AACTGGAGAG     240

CCAGCGGGAG  CTGCTTCTTG  ATCTGGCCAA  GAGAAGCATC  TTGGACAAGC  TGCACCTCAC     300

CCAGCGCCCA  ACACTGAACC  GCCCTGTGTC  CAGAGCTGCT  TTGAGGACTG  CACTGCAGCA     360

CCTCCACGGG  GTCCCACAGG  GGGCACTTCT  AGAGGACAAC  AGGGAACAGG  AATGTGAAAT     420

CATCAGCTTT  GCTGAGACAG  GCCTCTCCAC  CATCAACCAG  ACTCGTCTTG  ATTTTCACTT     480

CTCCTCTGAT  AGAACTGCTG  GTGACAGGGA  GGTCCAGCAG  GCCAGTCTCA  TGTTCTTTGT     540

GCAGCTCCCT  TCCAATACCA  CTTGGACCTT  GAAAGTGAGA  GTCCTTGTGC  TGGGTCCACA     600

TAATACCAAC  CTCACCTTGG  CTACTCAGTA  CCTGCTGGAG  GTGGATGCCA  GTGGCTGGCA     660

TCAACTCCCC  CTAGGGCCTG  AAGCTCAAGC  TGCCTGCAGC  CAGGGCACC   TGACCCTGGA     720

GCTGGTACTT  GAAGGCCAGA  TAGCCCAGAG  CTCAGTCATC  CTGGGTGGAG  CTGCCCATAG     780

GCCTTTTGTG  GCAGCCCGGG  TGAGAGTTGG  GGGCAAACAC  CAGATTCACC  GACGAGGCAT     840
```

-continued

| | | | | | |
|---|---|---|---|---|---|
| CGACTGCCAA | GGAGGGTCCA | GGATGTGCTG | TCGACAAGAG | TTTTTTGTGG | ACTTCCGTGA | 900 |
| GATTGGCTGG | CACGACTGGA | TCATCCAGCC | TGAGGGCTAC | GCCATGAACT | TCTGCATAGG | 960 |
| GCAGTGCCCA | CTACACATAG | CAGGCATGCC | TGGTATTGCT | GCCTCCTTTC | ACACTGCAGT | 1020 |
| GCTCAATCTT | CTCAAGGCCA | ACACAGCTGC | AGGCACCACT | GGAGGGGGCT | CATGCTGTGT | 1080 |
| ACCCACGGCC | CGGCGCCCCC | TGTCTCTGCT | CTATTATGAC | AGGGACAGCA | ACATTGTCAA | 1140 |
| GACTGACATA | CCTGACATGG | TAGTAGAGGC | CTGTGGGTGC | AGTTAGTCTA | TGTGTGGTAT | 1200 |
| GGGCAGCCCA | AGGTTGCATG | GGAAAACACG | CCCCTACAGA | AGTGCACTTC | CTTGAGAGGA | 1260 |
| GGGAATGACC | TCATTCTCTG | TCCAGAATGT | GGACTCCCTC | TTCCTGAGCA | TCTTATGGAA | 1320 |
| ATTACCCCAC | CTTTGACTTG | AAGAAACCTT | CATCTAAAGC | AAGTCACTGT | GCCATCTTCC | 1380 |
| TGACCACTAC | CCTCTTTCCT | AGGGCATAGT | CCATCCCGCT | AGTCCATCCC | GCTAGCCCCA | 1440 |
| CTCCAGGGAC | TCAGACCCAT | CTCCAACCAT | GAGCAATGCC | ATCTGGTTCC | CAGGCAAAGA | 1500 |
| CACCCTTAGC | TCACCTTTAA | TAGACCCCAT | AACCCACTAT | GCCTTCCTGT | CCTTTCTACT | 1560 |
| CAATGGTCCC | CACTCCAAGA | TGAGTTGACA | CAACCCCTTC | CCCCAATTTT | TGTGGATCTC | 1620 |
| CAGAGAGGCC | CTTCTTTGGA | TTCACCAAAG | TTTAGATCAC | TGCTGCCCAA | AATAGAGGCT | 1680 |
| TACCTACCCC | CCTCTTTGTT | GTGAGCCCCT | GTCCTTCTTA | GTTGTCCAGG | TGAACTACTA | 1740 |
| AAGCTCTCTT | TGCATACCTT | CATCCATTTT | TTGTCCTTCT | CTGCCTTTCT | CTATGCCCTT | 1800 |
| AAGGGGTGAC | TTGCCTGAGC | TCTATCACCT | GAGCTCCCCT | GCCCTCTGGC | TTCCTGCTGA | 1860 |
| GGTCAGGGCA | TTTCTTATCC | CTGTTCCCTC | TCTGTCTAGG | TGTCATGGTT | CTGTGTAACT | 1920 |
| GTGGCTATTC | TGTGTCCCTA | CACTACCTGG | CTACCCCCTT | CCATGGCCCC | AGCTCTGCCT | 1980 |
| ACATTCTGAT | TTTTTTTTTT | TTTTTTTTT | TGAAAAGTTA | AAAATTCCTT | AATTTTTTAT | 2040 |
| TCCTGGTACC | ACTACCACAA | TTTACAGGGC | AATATACCTG | ATGTAATGAA | AAGAAAAAGA | 2100 |
| AAAAGACAAA | GCTACAACAG | ATAAAAGACC | TCAGGAATGT | ACATCTAATT | GACACTACAT | 2160 |
| TGCATTAATC | AATAGCTGCA | CTTTTTGCAA | ACTGTGGCTA | TGACAGTCCT | GAACAAGAAG | 2220 |
| GGTTTCCTGT | TTAAGCTGCA | GTAACTTTTC | TGACTATGGA | TCATCGTTCC | TT | 2272 |

(2) INFORMATION FOR SEQ ID NO:2:

(i) SEQUENCE CHARACTERISTICS:
        (A) LENGTH: 352 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Thr Ser Ser Leu Leu Leu Ala Phe Leu Leu Leu Ala Pro Thr Thr
 1               5                  10                  15

Val Ala Thr Pro Arg Ala Gly Gly Gln Cys Pro Ala Cys Gly Gly Pro
            20                  25                  30

Thr Leu Glu Leu Glu Ser Gln Arg Glu Leu Leu Leu Asp Leu Ala Lys
        35                  40                  45

Arg Ser Ile Leu Asp Lys Leu His Leu Thr Gln Arg Pro Thr Leu Asn
    50                  55                  60

Arg Pro Val Ser Arg Ala Ala Leu Arg Thr Ala Leu Gln His Leu His
65                  70                  75                  80

Gly Val Pro Gln Gly Ala Leu Leu Glu Asp Asn Arg Glu Gln Glu Cys
                85                  90                  95

Glu Ile Ile Ser Phe Ala Glu Thr Gly Leu Ser Thr Ile Asn Gln Thr
```

|   |   |   |   |   |   |   |   |   |   |   |   |   |   |   |
|---|---|---|---|---|---|---|---|---|---|---|---|---|---|---|
|   |   |   |   | 100 |   |   |   | 105 |   |   |   | 110 |   |   |
| Arg | Leu | Asp<br>115 | Phe | His | Phe | Ser | Ser<br>120 | Asp | Arg | Thr | Ala | Gly<br>125 | Asp | Arg | Glu |
| Val | Gln<br>130 | Gln | Ala | Ser | Leu | Met<br>135 | Phe | Phe | Val | Gln | Leu<br>140 | Pro | Ser | Asn | Thr |
| Thr | Trp | Thr<br>145 | Leu | Lys | Val | Arg<br>150 | Val | Leu | Val | Leu | Gly<br>155 | Pro | His | Asn | Thr<br>160 |
| Asn | Leu<br>165 | Thr | Leu | Ala | Thr | Gln<br>170 | Tyr | Leu | Leu | Glu | Val<br>175 | Asp | Ala | Ser | Gly |
| Trp | His | Gln | Leu<br>180 | Pro | Leu | Gly | Pro | Glu<br>185 | Ala | Gln | Ala | Ala | Cys<br>190 | Ser | Gln |
| Gly | His | Leu<br>195 | Thr | Leu | Glu | Leu | Val<br>200 | Leu | Glu | Gly | Gln | Val<br>205 | Ala | Gln | Ser |
| Ser | Val<br>210 | Ile | Leu | Gly | Gly | Ala<br>215 | Ala | His | Arg | Pro | Phe<br>220 | Val | Ala | Ala | Arg |
| Val | Arg<br>225 | Val | Gly | Gly | Lys<br>230 | His | Gln | Ile | His | Arg<br>235 | Arg | Gly | Ile | Asp | Cys<br>240 |
| Gln | Gly | Gly | Ser | Arg<br>245 | Met | Cys | Cys | Arg | Glu<br>250 | Phe | Phe | Val | Asp | Phe<br>255 |
| Arg | Glu | Ile | Gly<br>260 | Trp | His | Asp | Trp | Ile<br>265 | Ile | Gln | Pro | Glu | Gly<br>270 | Tyr | Ala |
| Met | Asn | Phe<br>275 | Cys | Ile | Gly | Gln | Cys<br>280 | Pro | Leu | His | Ile | Ala<br>285 | Gly | Met | Pro |
| Gly | Ile | Ala<br>290 | Ala | Ser | Phe | His<br>295 | Thr | Ala | Val | Leu | Asn<br>300 | Leu | Leu | Lys | Ala |
| Asn | Thr<br>305 | Ala | Ala | Gly | Thr<br>310 | Thr | Gly | Gly | Gly | Ser<br>315 | Cys | Cys | Val | Pro | Thr<br>320 |
| Ala | Arg | Arg | Pro | Leu<br>325 | Ser | Leu | Leu | Tyr | Tyr<br>330 | Asp | Arg | Asp | Ser | Asn<br>335 | Ile |
| Val | Lys | Thr | Asp<br>340 | Ile | Pro | Asp | Met | Val<br>345 | Val | Glu | Ala | Cys | Gly<br>350 | Cys | Ser |

( 2 ) INFORMATION FOR SEQ ID NO:3:

( i ) SEQUENCE CHARACTERISTICS:
        ( A ) LENGTH: 1558 base pairs
        ( B ) TYPE: nucleic acid
        ( C ) STRANDEDNESS: single
        ( D ) TOPOLOGY: linear ( i i ) MOLECULE TYPE: DNA ( x ) PUBLICATION INFORMATION:
        ( H ) DOCUMENT NUMBER: US 08/289,222
        ( I ) FILING DATE: 12-AUG-1994

( x i ) SEQUENCE DESCRIPTION: SEQ ID NO:3:

| | | | | | |
|---|---|---|---|---|---|
| AAGGAGTCAT | GCCAGTCGGA | GGTCAGTCAC | ATTCCTCCCA | GGGTCCCTGG | TGCCCAGGAC | 60 |
| AGAGTTGAAG | CACTCCCGTT | GAGACCCTGA | ATATAGGCTT | TGGGTCCTTT | AAGGAGGCTA | 120 |
| TCCTCCAGCA | ATGGCCTCCT | CCTTGCTCCT | GGCTCTTCTG | TTCCTGACTC | CAACCACAGT | 180 |
| AGTGAACCCC | AAAACTGAGG | GTCCATGCCC | AGCATGTTGG | GGTGCCATCT | TTGACCTGGA | 240 |
| GAGCCAGCGG | GAGCTGCTTC | TCGATTTGGC | CAAGAAAAGT | ATCCTGGACA | AGCTGCACCT | 300 |
| CAGCCAGCGC | CCCATACTCA | GTCGGCCAGT | GTCCAGAGGG | GCTCTCAAGA | CCGCGCTGCA | 360 |
| GCGCCTCCGC | GGGCCTCGAC | GGGAAACCCT | GTTGGAGCAT | GACCAGAGAC | AAGAAGAATA | 420 |
| TGAGATCATC | AGCTTTGCTG | ACACAGACCT | CTCCAGCATC | AACCAGACCC | GGCTCGAGTT | 480 |

| | | | | | |
|---|---|---|---|---|---|
| CCACTTCTCT | GGTAGAATGG | CCAGTGGCAT | GGAGGTCCGG | CAGACCCGCT | TCATGTTCTT | 540 |
| CGTGCAGTTC | CCCCACAATG | CCACCCAGAC | CATGAATATA | AGAGTTCTTG | TGCTAAGACC | 600 |
| ATATGACACC | AACCTCACCT | TGACAAGTCA | GTACGTGGTG | CAGGTGAATG | CCAGTGGCTG | 660 |
| GTACCAGCTT | CTCCTGGGAC | CTGAAGCTCA | AGCTGCTTGC | AGCCAGGGAC | ACCTTACTCT | 720 |
| GGAGCTGGTA | CCAGAAAGCC | AGGTGGCCCA | CAGTTCCTTG | ATCCTGGGCT | GGTTTTCCCA | 780 |
| CAGGCCTTTT | GTGGCAGCCC | AGGTAAGGGT | TGAGGGCAAG | CATCGGGTTC | GCCGGCGAGG | 840 |
| TATCGATTGC | CAGGGGGGGT | CCAGGATGTG | CTGTCGACAA | GAGTTTTTTG | TAGACTTCCG | 900 |
| TGAGATTGGC | TGGAATGACT | GGATCATCCA | GCCTGAAGGC | TATGCCATGA | ACTTCTGCAC | 960 |
| TGGGCAGTGC | CCACTACATG | TGGCAGGCAT | GCCTGGCATC | TCTGCCTCCT | TTCACACTGC | 1020 |
| AGTGCTGAAT | CTGCTCAAAG | CCAACGCAGC | TGCTGGCACC | ACTGGCAGGG | GCTCGTGCTG | 1080 |
| CGTGCCTACA | TCTCGGCGCC | CTCTGTCTTT | GCTCTACTAT | GACAGGGACA | GCAACATTGT | 1140 |
| CAAGACGGAT | ATACCTGACA | TGGTGGTCGA | GGCCTGCGGG | TGTAGTTAGC | TTATGGGTGA | 1200 |
| TACAGGCTGC | CTGAGGTAGA | ATGGCCTTCC | TCAGGAAGGG | AAACTCTGTT | CCCACTTCTG | 1260 |
| TCCAGAATGG | AAACACCTTT | CTAAGCATGC | AGACATCCCT | CTGTGGACTT | CAGGGGATCC | 1320 |
| ACCTCTAAAG | AGAGTCACTA | GTGACCAACA | GCCTTTCTCT | CTCCTGGGAC | ATGGTTGACC | 1380 |
| CAGTACACCC | ATCCTCAGCC | TTAAGTTAGA | GGCTAATCGA | CTCCTACATA | TATATGTCAT | 1440 |
| TTTGTCCTAG | CAAACACCCC | TTAGCTCCCC | TTAGTCAACT | ATGTAATCTA | CTCTGCCTCC | 1500 |
| CTGACCCTGC | CACCGGAAGG | TTCCTATTCC | ACGATGATAT | GCCTAGTGT | CTCCCCTT | 1558 |

( 2 ) INFORMATION FOR SEQ ID NO:4:

( i ) SEQUENCE CHARACTERISTICS:
        ( A ) LENGTH: 352 amino acids
        ( B ) TYPE: amino acid
        ( C ) STRANDEDNESS: single
        ( D ) TOPOLOGY: linear ( i i ) MOLECULE TYPE: peptide ( x ) PUBLICATION INFORMATION:
        ( H ) DOCUMENT NUMBER: US 08/289,222
        ( I ) FILING DATE: 12-AUG-1994

( x i ) SEQUENCE DESCRIPTION: SEQ ID NO:4:

```
Met  Ala  Ser  Ser  Leu  Leu  Leu  Ala  Leu  Leu  Phe  Leu  Thr  Pro  Thr  Thr
 1              5                        10                       15

Val  Val  Asn  Pro  Lys  Thr  Glu  Gly  Pro  Cys  Pro  Ala  Cys  Trp  Gly  Ala
               20                        25                       30

Ile  Phe  Asp  Leu  Glu  Ser  Gln  Arg  Glu  Leu  Leu  Leu  Asp  Leu  Ala  Lys
               35                        40                       45

Lys  Ser  Ile  Leu  Asp  Lys  Leu  His  Leu  Ser  Gln  Arg  Pro  Ile  Leu  Ser
     50                        55                       60

Arg  Pro  Val  Ser  Arg  Gly  Ala  Leu  Lys  Thr  Ala  Leu  Gln  Arg  Leu  Arg
65                             70                       75                       80

Gly  Pro  Arg  Arg  Glu  Thr  Leu  Leu  Glu  His  Asp  Gln  Arg  Gln  Glu  Glu
                    85                        90                       95

Tyr  Glu  Ile  Ile  Ser  Phe  Ala  Asp  Thr  Asp  Leu  Ser  Ser  Ile  Asn  Gln
                    100                       105                      110

Thr  Arg  Leu  Glu  Phe  His  Phe  Ser  Gly  Arg  Met  Ala  Ser  Gly  Met  Glu
               115                       120                      125

Val  Arg  Gln  Thr  Arg  Phe  Met  Phe  Phe  Val  Gln  Phe  Pro  His  Asn  Ala
               130                       135                      140
```

| | | | | | | | | | | | | | | |
|---|---|---|---|---|---|---|---|---|---|---|---|---|---|---|
| Thr | Gln | Thr | Met | Asn | Ile | Arg | Val | Leu | Val | Leu | Arg | Pro | Tyr | Asp | Thr |
| 145 | | | | | 150 | | | | | 155 | | | | | 160 |
| Asn | Leu | Thr | Leu | Thr | Ser | Gln | Tyr | Val | Gln | Val | Asn | Ala | Ser | Gly |
| | | | | 165 | | | | 170 | | | | | 175 | |
| Trp | Tyr | Gln | Leu | Leu | Gly | Pro | Glu | Ala | Gln | Ala | Ala | Cys | Ser | Gln |
| | | | 180 | | | | 185 | | | | | 190 | | |
| Gly | His | Leu | Thr | Leu | Glu | Leu | Val | Pro | Glu | Ser | Gln | Val | Ala | His | Ser |
| | | 195 | | | | | 200 | | | | | 205 | | | |
| Ser | Leu | Ile | Leu | Gly | Trp | Phe | Ser | His | Arg | Pro | Phe | Val | Ala | Ala | Gln |
| | 210 | | | | | 215 | | | | | 220 | | | | |
| Val | Arg | Val | Glu | Gly | Lys | His | Arg | Val | Arg | Arg | Arg | Gly | Ile | Asp | Cys |
| 225 | | | | | 230 | | | | | 235 | | | | | 240 |
| Gln | Gly | Gly | Ser | Arg | Met | Cys | Cys | Arg | Gln | Glu | Phe | Phe | Val | Asp | Phe |
| | | | | 245 | | | | | 250 | | | | | 255 | |
| Arg | Glu | Ile | Gly | Trp | Asn | Asp | Trp | Ile | Ile | Gln | Pro | Glu | Gly | Tyr | Ala |
| | | | 260 | | | | | 265 | | | | | 270 | | |
| Met | Asn | Phe | Cys | Thr | Gly | Gln | Cys | Pro | Leu | His | Val | Ala | Gly | Met | Pro |
| | | 275 | | | | | 280 | | | | | 285 | | | |
| Gly | Ile | Ser | Ala | Ser | Phe | His | Thr | Ala | Val | Leu | Asn | Leu | Leu | Lys | Ala |
| | 290 | | | | | 295 | | | | | 300 | | | | |
| Asn | Ala | Ala | Ala | Gly | Thr | Thr | Gly | Arg | Gly | Ser | Cys | Cys | Val | Pro | Thr |
| 305 | | | | | 310 | | | | | 315 | | | | | 320 |
| Ser | Arg | Arg | Pro | Leu | Ser | Leu | Leu | Tyr | Tyr | Asp | Arg | Asp | Ser | Asn | Ile |
| | | | | 325 | | | | | 330 | | | | | 335 | |
| Val | Lys | Thr | Asp | Ile | Pro | Asp | Met | Val | Val | Glu | Ala | Cys | Gly | Cys | Ser |
| | | | 340 | | | | | 345 | | | | | 350 | | |

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

CAGGTAGGTC CATGGTCG                                            18

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CTTGATTTTT AACAGACC                                            18

( 2 ) INFORMATION FOR SEQ ID NO:7:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

AGAATTCGCA TGCCATGGTC GACGAAGCTT TTTTTTTTTT TTTT 44

(2) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

AGAATTCGCA TGCCATGGTC GACG 24

(2) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GGCTACGCCA TGAACTTCTG CATA 24

(2) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

ACATAGCAGG CATGCCTGGT ATTG 24

(2) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

ACATAGCAGG CATGCCTGGT ATTG 24

(2) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

CTGCAGCTGT GTTGGCCTTG AGA 23

( 2 ) INFORMATION FOR SEQ ID NO:13:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

ACGAATTCCG ACGAGGCATC GACTGC                                        26

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

GCGTCGACTA CCATGTCAGG TATGTC                                        26

( 2 ) INFORMATION FOR SEQ ID NO:15:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Met His His His His His His Lys Leu Glu Phe Ala Met
1                   5                           10

( 2 ) INFORMATION FOR SEQ ID NO:16:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

GAATTCGCCA TGGGCATCGA CTGCCAAGGA GG                                 32

( 2 ) INFORMATION FOR SEQ ID NO:17:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

CCGCTCGAGA AGCTTCAACT GCACCCACAG GC                                 32

( 2 ) INFORMATION FOR SEQ ID NO:18:

( i ) SEQUENCE CHARACTERISTICS:
        ( A ) LENGTH: 39 base pairs (B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:18:

CCCGGATCCG CTAGCACCAT GACCTCCTCA TTGCTTCTG          39

(2) INFORMATION FOR SEQ ID NO:19:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:19:

CCCTGTTGTC CTCTAGAAGT G          21

(2) INFORMATION FOR SEQ ID NO:20:

(i) SEQUENCE CHARACTERISTICS:
(A) LENGTH: 34 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:20:

GGATCCGAAT TCGGCTTGGA GTGTGATGGC AAGG          34

(2) INFORMATION FOR SEQ ID NO:21:

(i) SEQUENCE CHARACTERISTICS:
(A) LENGTH: 34 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:21:

GGATCCGAAT TCCTCTGGGA CCTGGCAACT CTAG          34

(2) INFORMATION FOR SEQ ID NO:22:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:22:

GAGAATTCCA RCARTTYTTY AT          22

(2) INFORMATION FOR SEQ ID NO:23:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA ( x i ) SEQUENCE DESCRIPTION: SEQ ID NO:23:

GCAAGCTTTR TAYTCRTCRT C 21

( 2 ) INFORMATION FOR SEQ ID NO:24:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
Cys Cys Arg Gln Glu Phe Phe Val Asp Phe Arg Glu Ile Gly Trp His
1               5                   10                  15

Asp Trp Ile Ile Gln Pro Glu Gly Tyr Ala Met Asn Phe Cys Ile Gly
            20                  25                  30

Gln Cys Pro Leu His Ile Ala Gly Met Pro Gly Ile Ala Ala Ser Phe
        35                  40                  45

His Thr Ala Val Leu Asn Leu Leu Lys Ala Asn Thr Ala Ala Gly Thr
        50                  55                  60

Thr Gly Gly Gly Ser Cys Cys Val Pro Thr Ala Arg Arg Pro Leu Ser
65                  70                  75                  80

Leu Leu Tyr Tyr Asp Arg Asp Ser Asn Ile Val Lys Thr Asp Ile Pro
                85                  90                  95

Asp Met Val Val Glu Ala Cys Gly Cys Ser
                100                 105
```

( 2 ) INFORMATION FOR SEQ ID NO:25:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
Cys Cys Lys Lys Gln Phe Phe Val Ser Phe Lys Asp Ile Gly Trp Asn
1               5                   10                  15

Asp Trp Ile Ile Ala Pro Ser Gly Tyr His Ala Asn Tyr Cys Glu Gly
            20                  25                  30

Glu Cys Pro Ser His Ile Ala Gly Thr Ser Gly Ser Ser Leu Ser Phe
        35                  40                  45

His Ser Thr Val Ile Asn His Tyr Arg Met Arg Gly His Ser Pro Phe
        50                  55                  60

Ala Asn Leu Lys Ser Cys Cys Val Pro Thr Lys Leu Arg Pro Met Ser
65                  70                  75                  80

Met Leu Tyr Tyr Asp Asp Gly Gln Asn Ile Ile Lys Lys Asp Ile Gln
                85                  90                  95

Asn Met Ile Val Glu Glu Cys Gly Cys Ser
                100                 105
```

( 2 ) INFORMATION FOR SEQ ID NO:26:

( i ) SEQUENCE CHARACTERISTICS:
        ( A ) LENGTH: 105 amino acids
        ( B ) TYPE: amino acid
        ( C ) STRANDEDNESS: single (D) TOPOLOGY: linear (i i) MOLECULE TYPE: peptide (x i) SEQUENCE DESCRIPTION: SEQ ID NO:26:

| Cys | Cys | Arg | Gln | Gln | Phe | Phe | Ile | Asp | Phe | Arg | Leu | Ile | Gly | Trp | Asn |
|---|---|---|---|---|---|---|---|---|---|---|---|---|---|---|---|
| 1 | | | | 5 | | | | | 10 | | | | | 15 | |

| Asp | Trp | Ile | Ile | Ala | Pro | Thr | Gly | Tyr | Tyr | Gly | Asn | Tyr | Cys | Glu | Gly |
|---|---|---|---|---|---|---|---|---|---|---|---|---|---|---|---|
| | | | 20 | | | | | 25 | | | | | 30 | | |

| Ser | Cys | Pro | Ala | Tyr | Leu | Ala | Gly | Val | Pro | Gly | Ser | Ala | Ser | Ser | Phe |
|---|---|---|---|---|---|---|---|---|---|---|---|---|---|---|---|
| | | 35 | | | | | 40 | | | | | 45 | | | |

| His | Thr | Ala | Val | Val | Asn | Gln | Tyr | Arg | Met | Arg | Gly | Leu | Asn | Pro | Gly |
|---|---|---|---|---|---|---|---|---|---|---|---|---|---|---|---|
| | 50 | | | | | 55 | | | | | 60 | | | | |

| Thr | Val | Asn | Ser | Cys | Cys | Ile | Pro | Thr | Lys | Leu | Ser | Thr | Met | Ser | Met |
|---|---|---|---|---|---|---|---|---|---|---|---|---|---|---|---|
| 65 | | | | | 70 | | | | | 75 | | | | | 80 |

| Leu | Tyr | Phe | Asp | Asp | Glu | Tyr | Asn | Ile | Val | Lys | Arg | Asp | Val | Pro | Asn |
|---|---|---|---|---|---|---|---|---|---|---|---|---|---|---|---|
| | | | | 85 | | | | | 90 | | | | | 95 | |

| Met | Ile | Val | Glu | Glu | Cys | Gly | Cys | Ala |
|---|---|---|---|---|---|---|---|---|
| | | | 100 | | | | | 105 |

(2) INFORMATION FOR SEQ ID NO:27:

(i) SEQUENCE CHARACTERISTICS:
(A) LENGTH: 105 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:27:

| Cys | His | Arg | Val | Ala | Leu | Asn | Ile | Ser | Phe | Gln | Glu | Leu | Gly | Trp | Glu |
|---|---|---|---|---|---|---|---|---|---|---|---|---|---|---|---|
| 1 | | | | 5 | | | | | 10 | | | | | 15 | |

| Arg | Trp | Ile | Val | Tyr | Pro | Pro | Ser | Phe | Ile | Phe | His | Tyr | Cys | His | Gly |
|---|---|---|---|---|---|---|---|---|---|---|---|---|---|---|---|
| | | | 20 | | | | | 25 | | | | | 30 | | |

| Gly | Cys | Gly | Leu | His | Ile | Pro | Pro | Asn | Leu | Ser | Leu | Pro | Val | Pro | Gly |
|---|---|---|---|---|---|---|---|---|---|---|---|---|---|---|---|
| | | 35 | | | | | 40 | | | | | 45 | | | |

| Ala | Pro | Pro | Thr | Pro | Ala | Gln | Pro | Tyr | Ser | Leu | Leu | Pro | Gly | Ala | Gln |
|---|---|---|---|---|---|---|---|---|---|---|---|---|---|---|---|
| | 50 | | | | | 55 | | | | | 60 | | | | |

| Pro | Cys | Cys | Ala | Ala | Leu | Pro | Gly | Thr | Met | Arg | Pro | Leu | His | Val | Arg |
|---|---|---|---|---|---|---|---|---|---|---|---|---|---|---|---|
| 65 | | | | | 70 | | | | | 75 | | | | | 80 |

| Thr | Thr | Ser | Asp | Gly | Gly | Tyr | Ser | Phe | Lys | Tyr | Glu | Thr | Val | Pro | Asn |
|---|---|---|---|---|---|---|---|---|---|---|---|---|---|---|---|
| | | | | 85 | | | | | 90 | | | | | 95 | |

| Leu | Leu | Thr | Gln | His | Cys | Ala | Cys | Ile |
|---|---|---|---|---|---|---|---|---|
| | | | 100 | | | | | 105 |

(2) INFORMATION FOR SEQ ID NO:28:

(i) SEQUENCE CHARACTERISTICS:
(A) LENGTH: 36 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:28:

ATGAATTCCC ATGGACCTGG GCTGGMAKGA MTGGAT    36

(2) INFORMATION FOR SEQ ID NO:29:

(i) SEQUENCE CHARACTERISTICS:

(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:29:

ACGTGGGGTG GAATGACTGG AT  22

(2) INFORMATION FOR SEQ ID NO:30:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:30:

ATATTGGCTG GAGTGAATGG AT  22

(2) INFORMATION FOR SEQ ID NO:31:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:31:

ATGTGGGCTG GAATGACTGG AT  22

(2) INFORMATION FOR SEQ ID NO:32:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:32:

ACCTGGGCTG GCAGGACTGG AT  22

(2) INFORMATION FOR SEQ ID NO:33:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:33:

AGGACCTCGG CTGGAAGTGG AT  22

(2) INFORMATION FOR SEQ ID NO:34:

(i) SEQUENCE CHARACTERISTICS:
(A) LENGTH: 22 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:34:

GGGATCTAGG GTGGAAATGG AT                    22

( 2 ) INFORMATION FOR SEQ ID NO:35:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

AGGATCTGGG CTGGAAGTGG GT                    22

( 2 ) INFORMATION FOR SEQ ID NO:36:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

AGCTGGGCTG GGAACGGTGG AT                    22

( 2 ) INFORMATION FOR SEQ ID NO:37:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:37:

ACATCGGCTG GAATGACTGG AT                    22

( 2 ) INFORMATION FOR SEQ ID NO:38:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:38:

TCATCGGCTG GAACGACTGG AT                    22

( 2 ) INFORMATION FOR SEQ ID NO:39:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:39:

ATGAATTCGA GCTGCGTSGG SRCACAGCA             29

( 2 ) INFORMATION FOR SEQ ID NO:40:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

GAGTTCTGTC GGGACACAGC A         21

( 2 ) INFORMATION FOR SEQ ID NO:41:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

CATCTTTTCT GGTACACAGC A         21

( 2 ) INFORMATION FOR SEQ ID NO:42:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

CAGTTCAGTG GGCACACAAC A         21

( 2 ) INFORMATION FOR SEQ ID NO:43:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GAGCTGCGTG GGCGCACAGC A         21

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CAGCGCCTGC GGCACGCAGC A         21

( 2 ) INFORMATION FOR SEQ ID NO:45:

( i ) SEQUENCE CHARACTERISTICS:

( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: DNA ( x i ) SEQUENCE DESCRIPTION: SEQ ID NO:45:

TAAATCTTGG GACACGCAGC A                        21

( 2 ) INFORMATION FOR SEQ ID NO:46:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: DNA ( x i ) SEQUENCE DESCRIPTION: SEQ ID NO:46:

CAGGTCCTGG GGCACGCAGC A                        21

( 2 ) INFORMATION FOR SEQ ID NO:47:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: DNA ( x i ) SEQUENCE DESCRIPTION: SEQ ID NO:47:

CCCTGGGAGA GCAGCACAGC A                        21

( 2 ) INFORMATION FOR SEQ ID NO:48:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: DNA ( x i ) SEQUENCE DESCRIPTION: SEQ ID NO:48:

CAGCTTGGTG GGCACACAGC A                        21

( 2 ) INFORMATION FOR SEQ ID NO:49:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: DNA ( x i ) SEQUENCE DESCRIPTION: SEQ ID NO:49:

CAGCTTGGTG GGAATGCAGC A                        21